(12) United States Patent
Marshall

(10) Patent No.: US 8,787,626 B2
(45) Date of Patent: Jul. 22, 2014

(54) OMNIGENE SOFTWARE SYSTEM

(76) Inventor: Roger G. Marshall, Plymouth, NH (US)

( * ) Notice: Subject to any disclaimer, the term of this patent is extended or adjusted under 35 U.S.C. 154(b) by 0 days.

(21) Appl. No.: 13/476,001

(22) Filed: May 21, 2012

(65) Prior Publication Data

US 2013/0308833 A1    Nov. 21, 2013

(51) Int. Cl.
*G06K 9/00*    (2006.01)
(52) U.S. Cl.
USPC .......................................... 382/115; 382/128
(58) Field of Classification Search
None
See application file for complete search history.

(56) References Cited

U.S. PATENT DOCUMENTS

| | | | | |
|---|---|---|---|---|
| 5,733,729 | A * | 3/1998 | Lipshutz et al. | 435/6.11 |
| 7,106,329 | B1 * | 9/2006 | Miller et al. | 345/440 |
| 7,732,138 | B2 * | 6/2010 | Tam | 435/6.11 |
| 8,189,892 | B2 * | 5/2012 | Dimirova et al. | 382/129 |
| 2009/0129647 | A1 * | 5/2009 | Dimitrova et al. | 382/129 |
| 2009/0319591 | A1 * | 12/2009 | Allen et al. | 708/250 |
| 2011/0280466 | A1 * | 11/2011 | Cho et al. | 382/133 |

\* cited by examiner

*Primary Examiner* — Daniel Mariam

(57) ABSTRACT

A software system which employs a special set of simulated electrical circuits to generate user-specific textured and signature color images based on DNA, speech, fingerprint and retinal scans. The output of the system can be used in a variety of applications including easy visual identification of different types of gene sequences (human, plant, diseased, normal, etc.), drug design, multi-level security ID cards based on biometric data, custom colors and textures for diverse home and office products such as clothing, bedspreads, linen, stationery and fabric.

14 Claims, 32 Drawing Sheets

| Number of impedances | Connection strategy | | Notes |
|---|---|---|---|
| Two (X, Y) | Serial<br>X + Y | Parallel<br>X \|\| Y | Both are symmetric;<br>X+Y same as Y+X;<br>X \|\| same as Y \|\|X |
| Three (X, Y, Z) | Serial-parallel<br>(X+Y) \|\| Z | Parallel-serial<br>(X \|\| Y) + Z | Both asymmetric and both relevant to DNA modeling since DNA sequences are direction-specific |

Impedance interconnection

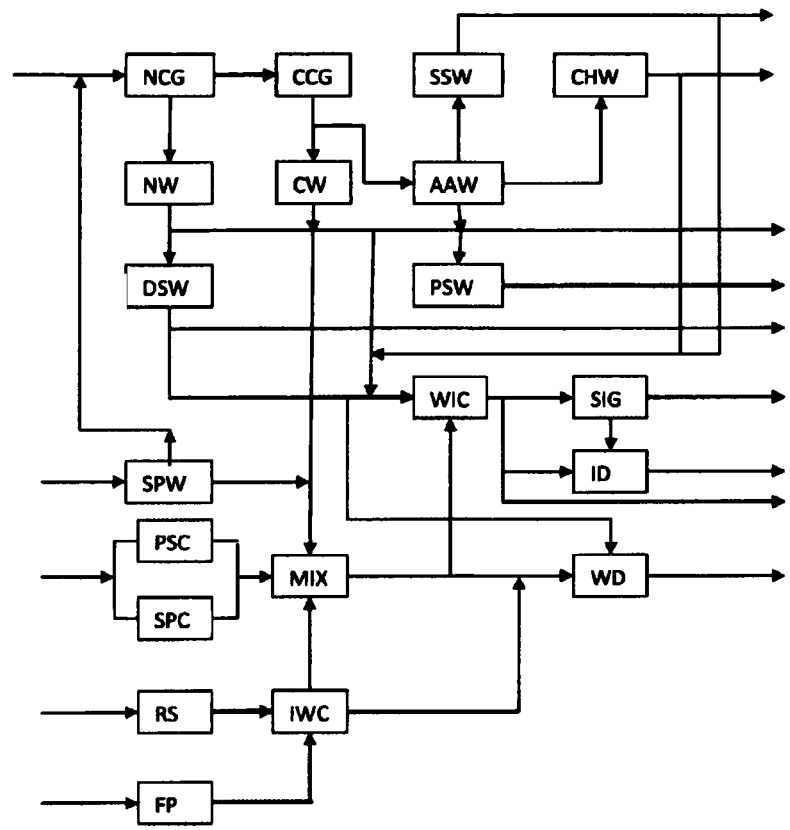

| LEGEND | | | | | |
|---|---|---|---|---|---|
| AAW | AMINO ACID WAVE | CCG | CODON CIRCUIT GENERATOR | CW | CODON WAVE |
| CHW | CHEMICAL ROPERTY WAVE | DSW | DNA SEQUENCE WAVE | FP | FINGERPRINT |
| ID | IMAGE DIFFERENCER | IWC | IMAGE TO WAVE CONVERTER | MIX | WAVE MIXER |
| NCG | NUCLEOTIDE IRCUIT GENERATOR | NW | NUCLEOTIDE WAVE | PSC | PARALLEL-SERIAL CIRCUIT |
| PSW | PROTEIN SEQUENCE WAVE | RS | RETINAL SCAN | SIG | SIGNATURE GENERATOR |
| SPC | SERIAL-PARALLEL CIRCUIT | SPW | SPEECH WAVE | SSW | SECONDARY STRUCTURE WAVE |
| WD | WAVE DIFFERENCER | WIC | WAVE TO IMAGE CONVERTER | | |

FIG. 1A Block Schematic of OMNIGENE System Operation

Notes: Five external inputs to the system on the left: - two sets of circuit parameters, one set to NCG, the other to PSC/SPC; Retinal Scan Image to RS; Speech Wave to SP; and Fingerprint Image to FP.
Nine system outputs on the right (in top to bottom order): -wave output from SSW, wave output from CHW, wave output from NW or CW or AAW, wave output from PSW, wave output from DSW, signature image from SIG, difference image from ID, textured image from WIC, and difference image from WD FIG. 1B Block Schematic of OMNIGENE System Operation

| Number of impedances | Connection strategy | | Notes |
|---|---|---|---|
| Two (X, Y) | Serial X + Y | Parallel X \|\| Y | Both are symmetric; X+Y same as Y+X; X \|\| same as Y \|\|X |
| Three (X, Y, Z) | Serial-parallel (X+Y) \|\| Z | Parallel-serial (X \|\| Y) + Z | Both asymmetric and both relevant to DNA modeling since DNA sequences are direction-specific |

FIG. 2 Impedance interconnection

| Nucleotide | Circuit model | Circuit element parameters |
|---|---|---|
| Adenosine (A) | Resistors R | $R_1 + 3R_2$ (labeled 'a') |
| Guanine (G) | Resistor and Inductor L in series | a, L1 |
| Cytosine (C) | Inductor and Capacitor in parallel | L2, g where g is inverse of capacitance |
| Thymine (T) | Series combination of the circuit models for Guanine and Thymine | a, L1, L2, g |

FIG. 3 Nucleotide (or base) circuit models

| Base | Circuit impedance in Laplacian terms | |
|---|---|---|
| | Numerator $N_0$ | Denominator $D_0$ |
| A | a | 1 |
| C | $(s^2 L_2 R_2 + sgL_2 + gR_2)$ | $(s^2 L_2 + g)$ |
| G | $(sL_1 + a)$ | 1 |
| T | $[s^3 L_1 L_2 + s^2 L_2 R_1 + sg(L_1 + L_2) + gR_1]$ | $(s^2 L_2 + g)$ |

FIG. 4 Nucleotide circuit impedance

PARALLEL - SERIAL CIRCUIT MODEL

| Doublet | Circuit impedance expression (N / D) | |
|---|---|---|
| | Numerator N | Denominator D |
| AA | a | 2 |
| AG | $a(sL_1 + a)$ | $(sL_1 + 2a)$ |

FIG. 5A Impedance expressions for doublet circuits (parallel - serial version)

| | | |
|---|---|---|
| AT | $a[s^3 L_1L_2 + s^2 L_2R_1 + sg(L_1+L_2) + gR_1]$ | $[s^3 L_1L_2 + s^2 L_2(a + R_1) + sg(L_1+L_2) + g(a + R_1)]$ |
| AC | $a[s^2 L_2R_2 + sgL_2 + gR_2]$ | $[s^2 L_2(a + R_2) + sgL_2 + g(a + R_2)]$ |
| | | |
| GA | same as AG | same as AG |
| GG | $(sL_1 + a)$ | 2 |
| GT | $[s^4 L_1^2 L_2 + s^3 L_1L_2 (a + R_1) + s^2(aL_2R_1 + gL_1(L_1+L_2)) + sg(a(L_1+L_2) + L_1R_1) + agR_1]$ | $[2s^3 L_1L_2 + s^2 L_2(a+R_1) + sg(2L_1 + L_2)) + g(a + R_1)]$ |
| GC | $[s^3 L_1 L_2R_2 + s^2 L_2(aR_2 + gL_1) + sgL_1R_2 + agR_2]$ | $[s^3 L_1L_2 + s^2 L_2(a + R_2) + sg(L_1 + L_2) + g(a + R_2)]$ |
| | | |
| TA | same as AT | same as AT |
| TG | same as GT | same as GT |
| TT | $[s^3 L_1L_2 + s^2 L_2R_1 + sg(L_1+L_2) + gR_1]$ | $2(s^2 L_2 + g)$ |
| TC | $[s^5 L_1L_2^2 R_2 + s^4 L_2^2(gL_1 + R_1R_2) + s^3 gL_2[2L_1R_1 + L_2R_2 + L_1R_2] + s^2 gL_2[2R_1R_2 + g(L_1+L_2)] + sg^2[R_1L_2+L_1R_2+L_2R_2] + g^2R_1R_2]$ | $[s^5 L_1L_2^2 + s^4 L_2^2(R_1 + R_2) + 2s^3 gL_2(L_1+L_2) + 2s^2 gL_2(R_1 + R_2) + sg^2(L_1+2L_2) + g^2(R_1 + R_2)]$ |
| | | |
| CA | same as AC | same as AC |
| CG | same as GC | same as GC |
| CT | same as TC | same as TC |
| CC | $(s^2 L_2R_2 + gL_2s + gR_2)$ | $2(s^2 L_2 + g)$ |

FIG. 5B Impedance expressions for doublet circuits (parallel − serial version)

| Codon | Circuit impedance expression (N / D) | |
|---|---|---|
| | Numerator N | Denominator D |
| AAA | $3a$ | 2 |
| AAG | $(2sL_1 + 3a)$ | 2 |
| AAT | $[2s^3 L_1L_2 + s^2 L_2(a + 2R_1) + 2sg(L_1 + L_2) + g(a + 2R_1)]$ | $2(s^2L_2 + g)$ |
| AAC | $[2s^2 L_2(a + 2R_2) + 2sgL_2 + g(a + 2R_2)]$ | $2(s^2L_2 + g)$ |
| | | |
| AGA | $a(3a + 2sL_1)$ | $(sL_1 + 2a)$ |
| AGG | $(s^2L_1^2 + 4saL_1 + 3a^2)$ | $(sL_1 + 2a)$ |

FIG. 6A Impedance expressions for the codon circuit model (parallel − serial version)

| | | |
|---|---|---|
| AGT | $s^4L_1^2L_2 + s^3L_1L_2(3a + R_1) + s^2[L_2(3aR_1 + gL_1) + gL_1^2] + sg[L_1(3a + R_1) + 2aL_2] + 2ag(a + R_1)$ | $(s^3L_1L_2 + 2s^2aL_2 + sgL_1 + 2ag)$ |
| AGC | $s^3L_1L_2(a + R_2) + s^2L_2(a^2 + 2aR_2 + gL_1) + sg(aL_1 + 2aL_2 + L_1R_2) + 2ag(a + R_2)$ | $(s^3L_1L_2 + 2s^2aL_2 + sgL_1 + 2ag)$ |
| ATA | $a[2s^3L_1L_2 + s^2L_2(a + 2R_1) + 2sg(L_1+L_2) + g(a + 2R_1)]$ | $[s^3 L_1L_2 + s^2 L_2(a + R_1) + sg(L_1+L_2) + g(a + R_1)]$ |
| ATG | $[s^4 L_1^2L_2 + s^3 L_1 L_2(3a + R_1) + s^2[L_1 g(L_1+L_2) + a L_2(a + 2R_1)] + sg[L_1(3a + R_1) + 2aL_2] + ag(a + 2R_1)]$ | $[s^3 L_1L_2 + s^2 L_2(a + R_1) + sg(L_1+L_2) + g(a + R_1)]$ |
| ATT | $\{s^6 L_1^2L_2^2 + s^5 L_1L_2^2 (a + 3R_1) + s^4 L_2[2gL_1(L_1+L_2) + R_1(L_2R_1 + aL_1 + aL_2)] + s^3gL_2(a + R_1)(3L_1 + aL_2) + s^2 g[g(L_1^2+2L_1L_2 + L_2^2) + 2R_1L_2(2a + R_1)] + 2s g^2(L_2 + L_1)(a + R_1) + g^2R_1(2a + R_1)\}$ | $[s^5 L_1L_2^2 + s^4 L_2^2 (a + R_2) + s^3 gL_2 (2L_1 + L_2) + 2s^2 g(a + R_2) + sg^2(L_1 + L_2) + g^2(a + R_2)]$ |
| ATC | $\{s^5 L_1L_2^2(a + R_2) + s^4L_2[L_2R_2(a + R_1) + gL_2L_1 + aL_1R_1] + s^3gL_2[(a + R_2)(2L_1 + L_2) + L_2(a + R_1)] + s^2gL_2[2aR_1 + g(L_1+L_2) + 2R_2(a + R_1)] + sg^2[L_2(a + R_1) + (a + R_2)(L_1 + L_2)] + g^2[R_1R_2 + a(R_1 + R_2)]\}$ | $[s^5 L_1L_2^2 + s^4 L_2^2 (a + R_2) + s^3 gL_2 (2L_1 + L_2) + 2s^2 g(a + R_2) + sg^2(L_1 + L_2) + g^2(a + R_2)]$ |
| ACA | $a[s^2L_2(a + 2R_2) + sgL_2 + g(a + 2R_2)]$ | $[s^2L_2(a + R_2) + sgL_2 + g(a + R_2)]$ |
| ACG | $s^3L_1L_2(a + R_2) + s^2L_2[a(a + 2R_2) + gL_1] + sg[2aL_2 + L_1(a + R_2)] + ag(a + 2R_2)$ | $[s^2L_2(a + R_2) + sgL_2 + g(a + R_2)]$ |
| ACT | $\{s^5 L_1L_2^2(a + R_2) + s^4 L_2^2 [gL_1 + (a +2R_2)R_1] + s^3 gL_2[ 2(a + R_2) L_1 + (2a + R_1 + R_2) L_2 )] + s^2 gL_2 [2(a + R_2) R_1 + g(L_1 + L_2) + 2aR_2] + s g^2 [2aL_2 + aL_1 + R_2L_2 + 2L_2R_1] + g^2[aR_2 + (a + R_2)R_1]\}$ | $[s^4L_2^2(a + R_2) + s^3 gL_2^2 + 2s^2gL_2(a + R_2) + sgL_2^2 + g^2(a + R_2)]$ |
| ACC | $\{s^4L_2^2R_2(2a + R_2) + 2s^3gL_2^2(a + R_2) + s^2gL_2 [(2a + R_2) R_2 + gL_2] + 2sg^2L_2 (a + R_2) + g^2R_2(2a + R_2)\}$ | $[s^4L_2^2(a + R_2) + s^3 gL_2^2 + 2s^2gL_2(a + R_2) + sgL_2^2 + g^2(a + R_2)]$ |
| GAA | same as AGA | same as AGA |
| GAG | same as AGG | same as AGG |
| GAT | same as AGT | same as AGT |

FIG. 6B Impedance expressions for the codon circuit model (parallel - serial version)

| | | |
|---|---|---|
| GAC | same as AGC | same as AGC |
| GGA | $(sL_1 + 3a)$ | 2 |
| GGG | $3(sL_1 + a)$ | 2 |
| GGT | $[3s^3 L_1L_2 + s^2 L_2(a + 2R_1) + sg(2L_1 + L_2) + g(a + 2R_1)]$ | $2(s^2L_2 + g)$ |
| GGC | $[s^3L_1L_2 + s^2L_2(a + 2R_2) + sg(L_1 + 2L_2) + g(a + 2R_2)]$ | $2(s^2L_2 + g)$ |
| GTA | $\{s^4L_1{}^2L_2 + s^3L_1L_2 (3a + R_1) + s^2[aL_2(a + 2R_1) + gL_1(L_1+L_2)] + sg[a(3L_1+2L_2) + L_1R_1] + ag(a + 2R_1)\}$ | $[2s^3L_1L_2 + s^2 L_2(a+R_1) + sg(2L_1+ L_2)) + g(a+R_1)]$ |
| GTG | $[3s^4L_1{}^2L_2 + s^3L_1L_2 (3a + 2R_1) + s^2aL_2[(a + 2R_1) + gL_1(3L_1+2L_2)] + sg[2L_1(2a + R_1) + 2aL_2) + 2ag(a + 2R_1)]$ | $[2s^3L_1L_2 + s^2L_2(a+R_1) + sg(2L_1 + L_2)) + g(a+ R_1)]$ |
| GTT | $\{3s^6L_1{}^2L_2{}^2 + 2s^5L_1L_2{}^2 (a + 2R_1) + s^4L_2[L_2R_1(2a + R_1) + 2gL_1(3L_1 + 2L_2)] + s^3gL_2[L_1(3a + 7R_1) + 2L_2(a + R_1)] + s^2g[2L_2R_1(2a + R_1) + g(L_1 + L_2)(3L_1 + L_2)] + sg^2(a + R_1)(2L_1 + L_2) + g^2R_1(2a + R_1)\}$ | $[2s^5 L_1L_2{}^2 + s^4 L_2{}^2 (a + R_1) + s^3 gL_2 (4L_1 + L_2) + 2s^2 gL_2(a + R_1) + sg^2(2L_1 + L_2) + g^2(a + R_1)]$ |
| GTC | $\{3s^6L_1{}^2L_2{}^2 + 2s^5L_1L_2{}^2 (a + 2R_1) + s^4L_2[L_2R_1(2a + R_1) + 2gL_1(3L_1 + 2L_2)] + s^3gL_2[L_1(3a + 7R_1) + 2L_2(a + R_1)] + s^2g[2L_2R_1(2a + R_1) + g(L_1 + L_2)(3L_1 + L_2)] + sg^2(a + R_1)(2L_1 + L_2) + g^2R_1(2a + R_1)\}$ | $[2s^5 L_1L_2{}^2 + s^4 L_2{}^2 (a + R_1) + s^3 gL_2 (4L_1 + L_2) + 2s^2 gL_2(a + R_1) + sg^2(2L_1 + L_2) + g^2(a + R_1)]$ |
| GCA | $[s^3L_1L_2(a+R_2)+s^2L_2(a^2 +2aR_2+ gL_1)+sg[L_1R_2 +a(L_1 + L_2)]+ag(a +2R_2)]$ | $[s^3L_1L_2 + s^2L_2(a +R_2) +sg(L_1 + L_2) + g(a + R_2)]$ |
| GCG | $\{2s^4 L_1{}^2 L_2 + 2s^3 L_1 L_2(a + R_2) + s^2 [2L_1 g(L_1 + L_2) + a L_2(a + 2R_2)] + sg[L_1(3a + 2R_2) + aL_2)] + a g(a + 2R_2)\}$ | $[s^3L_1L_2 + s^2L_2(a +R_2) +sg(L_1 + L_2) + g(a + R_2)]$ |
| GCT | $\{s^6L_1{}^2L_2{}^2 + s^5L_1L_2{}^2(a + R_1 + 2R_2) + s^4L_2\{L_2[R_1(a + R_2) + aR_2] + gL_1(2L_1 + 3L_2)\} + s^3gL_2[R_2(3L_1 + L_2) + (a + R_1)(L_1 + L_2)] + s^2g\{2L_2[a(R_1 + R_2) + R_1R_2] + g(L_1{}^2 + 3L_1L_2 + L_2{}^2)\} + sg^2[(a + R_1)(L_1 + L_2) + R_2(2L_1 + L_2)] + g^2[a(R_1 + R_2) + R_1R_2]\}$ | $[s^5 L_1L_2{}^2 + s^4 L_2{}^2 (a + R_2) + s^3 gL_2 (2L_1 + L_2) + 2s^2 g(a + R_2) + sg^2(L_1 + L_2) + g^2(a + R_2)]$ |

FIG. 6C Impedance expressions for the codon circuit model

| | (parallel - serial version) | |
|---|---|---|
| GCC | $\{2s^5 L_1L_2^2 R_2 + s^4 L_2^2 [R_2 (2a + R_2) + 2gL_1] + s^3 gL_2 [3R_2 (L_1 + L_2) + aL_2 ] + s^2 gL_2[2R_2(2a + R_2) + g(2L_1 + L_2)] + sg^2[(a + 3R_2)L_2 + R_2 L_1] + g^2R_2 (2a + R_2)\}$ | $[s^5 L_1L_2^2 + s^4 L_2^2 (a + R_2) + s^3 gL_2 (2L_1 + L_2) + 2s^2 g(a + R_2) + sg^2(L_1 + L_2) + g^2(a + R_2)]$ |
| TAA | same as ATA | same as ATA |
| TAG | same as ATG | same as ATG |
| TAT | same as ATT | same as ATT |
| TAC | same as ATC | same as ATC |
| TGA | same as GTA | same as GTA |
| TGG | same as GTG | same as GTG |
| TGT | same as GTT | same as GTT |
| TGC | same as GTC | same as GTC |
| TTA | $[s^3 L_1L_2 + s^2 L_2 (2a + R_1) + sg(L_1+L_2) + g(2a + R_1)]$ | $2(s^2 L_2 + g)$ |
| TTG | $[3s^3 L_1L_2 + s^2 L_2(2a + R_1) + sg(3L_1+L_2) + g(2a + R_1)]$ | $2(s^2 L_2 + g)$ |
| TTT | $3[ s^2 L_2R_1 + sg(L_1 + L_2) + gR_1]$ | $2(s^2L_2 + g)$ |
| TTC | $[s^3 L_1L_2 + s^2 L_2(R_1 + 2R_2) + sg(L_1+3L_2) + g(R_1 + 2R_2)]$ | $2(s^2L_2 + g)$ |
| TCA | $\{s^5 L_1L_2^2(a + R_2) + s^4L_2^2(gL_1 + aR_1 + aR_2 + R_1R_2) + s^3gL_2[2L_1R_1+2aL_1 + 2aL_2 + L_2R_2+ L_1R_2] + s^2gL_2[2R_1R_2 + g(L_1+L_2) + 2aR_1 + 2aR_2] + sg^2[R_1L_2+L_1R_2+L_2R_2 + aL_1 + 2aL_2] + g^2[R_1R_2 + a(R_1+ R_2)]\}$ | $[s^5L_1L_2^2 + s^4L_2^2(R_1 + R_2)+2s^3gL_2(L_1+L_2) + 2s^2gL_2 (R_1+ R_2) + sg^2(L_1+2L_2) + g^2(R_1+ R_2)]$ |
| TCG | $\{s^6 L_1^2L_2^2 + s^5 L_1L_2^2 (a + R_1 + 2R_2) + s^4 L_2[gL_1(2L_1+3L_2) + L_2(R_1R_2 + aR_1 + aR_2)] + s^3gL_2[(2a + 4R_1+ 3R_2)L_1 +(2a + R_2)L_2] + s^2 g[ g(L_1^2+3L_1L_2 + L_2^2 ) + 2aL_2(R_1+ R_2)+ 2L_2R_1R_2] + s g^2[R_1(L_2 + L_1) + R_2 (2L_1 +L_2) + a(L_1+2L_2)] + g^2(R_1R_2 + aR_1+ aR_2)\}$ | $[s^5L_1L_2^2 + s^4L_2^2(R_1 + R_2)+2s^3gL_2(L_1+L_2) + 2s^2gL_2 (R_1+ R_2) + sg^2(L_1+2L_2) + g^2(R_1+ R_2)]$ |

FIG. 6D Impedance expressions for the codon circuit model (parallel - serial version)

| | | |
|---|---|---|
| TCT | $s^8 L_1^2 L_2^3 + 2s^7 L_1 L_2^3 (R_1 + R_2) + s^6 L_2^2 [L_2 R_1 (R_1 + 2R_2) + gL_1 (3L_1 + 4L_2)] + s^5 gL_2^2 [5L_1 (R_1 + R_2) + L_2 (R_1 + 2R_2)] + s^4 gL_2 [3L_2 R_1 (R_1 + 2R_2) + g(3L_1^2 + 8L_1 L_2 + 3L_2^2)] + s^3 g^2 L_2 [L_1 (6R_1 + 5R_2) + g(L_1 + L_2)(L_1 + 3L_2)] + s^2 g^2 [3L_2 R_1 (R_1 + 2R_2) + g(L_1 + L_2)(L_1 + 3L_2)] + sg^3 [2(L_1 R_2 + L_2 R_1 + L_2 R_2) + L_1 R_1] + g^3 R_1 (R_1 + 2R_2)$ | $s^7 L_1 L_2^3 + s^6 L_2^3 (R_1 + R_2) + s^5 L_2^2 g (3L_1 + 2L_2) + s^4 gL_2^2 (3R_1 + 2R_2) + s^3 g^2 L_2 (3L_1 + 4L_2) + s^2 g^2 L_2 (2R_1 + 3R_2) + s g^3 (L_1 + 2L_2) + g^3 (R_1 + R_2)$ |
| TCC | $2s^7 L_1 L_2^3 R_2 + s^6 L_2^3 [(2R_1 + R_2) R_2 + 2L_1 g] + s^5 gL_2^2 [2L_1 R_1 + L_2 (R_1 + 4R_2) + 5L_1 R_2] + s^4 gL_2^2 [3R_2 (2R_1 + R_2) + g(4L_1 + 3L_2)] + s^3 g^2 L_2 [R_2 (5L_1 + 6L_2) + L_2 (5R_1 + 2R_2)] + s^2 g^2 L_2 [3(2R_1 + R_2) R_2 + g(2L_1 + 3L_2)] + 2sg^3 [(R_1 + 2R_2) L_2 + L_1 R_2] + g^3 R_2 (2R_1 + R_2)$ | $s^7 L_1 L_2^3 + s^6 L_2^3 (R_1 + R_2) + s^5 L_2^2 g (3L_1 + 2L_2) + s^4 gL_2^2 (3R_1 + 2R_2) + s^3 g^2 L_2 (3L_1 + 4L_2) + s^2 g^2 L_2 (2R_1 + 3R_2) + s g^3 (L_1 + 2L_2) + g^3 (R_1 + R_2)$ |
| CAA | same as ACA | same as ACA |
| CAG | same as ACG | same as ACG |
| CAT | same as ACT | same as ACT |
| CAC | same as ACC | same as ACC |
| CGA | same as GCA | same as GCA |
| CGG | same as GCG | same as GCG |
| CGT | same as GCT | same as GCT |
| CGC | same as GCC | same as GCC |
| CTA | same as TCA | same as TCA |
| CTG | same as TCG | same as TCG |
| CTT | same as TCT | same as TCT |
| CTC | same as TCC | same as TCC |
| CCA | $(s^2 L_2 (2a + R_2) + gL_2 s + g(2a + R_2))$ | $2(s^2 L_2 + g)$ |
| CCG | $(2s^3 L_1 L_2 + s^2 L_2 (2a + R_2) + sg(2L_1 + L_2) + g(2a + R_2))$ | $2(s^2 L_2 + g)$ |
| CCT | $[2s^3 L_1 L_2 + s^2 L_2 (2R_1 + R_2) + sg(2L_1 + 3L_2) + g(2R_1 + R_2)]$ | $2(s^2 L_2 + g)$ |
| CCC | $3[s^2 L_2 R_2 + sgL_2 + gR_2]$ | $2(s^2 L_2 + g)$ |

FIG. 6E Impedance expressions for the codon circuit model
(parallel – serial version)

SERIAL - PARALLEL CIRCUIT MODEL

| Codon | Circuit impedance expression N / D | |
|---|---|---|
| | Numerator N | Denominator D |
| AA | $2a$ | $1$ |
| AG | $(sL_1 + 2a)$ | $1$ |
| AT | $[s^3 L_1L_2 + s^2L_2 (R_1+ a) + sg(L_1+L_2) + g(R_1+ a)]$ | $(s^2 L_2 + g)$ |
| AC | $[s^2 L_2(a + R_2) + sgL_2 + g(a + R_2)]$ | $(s^2 L_2 + g)$ |
| | | |
| GA | same as AG | same as AG |
| GG | $2(sL_1 + a)$ | $1$ |
| GT | $[2s^3L_1L_2 + s^2 L_2(R_1+ a) + sg(2L_1 + L_2) + g(a+R_1)]$ | $(s^2 L_2 + g)$ |
| GC | $[s_3L_1L_2 + s^2 L_2(R_2 + a) + sg(L_1 + L_2) + g(a + R_2)]$ | $(s^2 L_2 + g)$ |
| | | |
| TA | same as AT | same as AT |
| TG | same as GT | same as GT |
| TT | $2[s^3 L_1L_2 + s^2 L_2R_1 + sg(L_1+L_2) + gR_1]$ | $(s^2 L_2 + g)$ |
| TC | $[s^3L_1L_2 + s^2L_2(R_1 + R_2) + sg(L_1+2L_2) + g(R_1+R_2)]$ | $(s^2 L_2 + g)$ |
| | | |
| CA | same as AC | same as AC |
| CG | same as GC | same as GC |
| CT | same as TC | same as TC |
| CC | $2(s^2 L_2R_2 + gL_2s + gR_2)$ | $(s^2 L_2 + g)$ |

FIG. 7 Impedance expressions for the doublet circuit model (serial - parallel version)

| Codon | Circuit impedance expression (N / D) | |
|---|---|---|
| | Numerator N | Denominator D |
| AAA | $2a^2$ | $3a$ |
| AAG | $[2a(sL_1 + a)]$ | $[(sL_1 + 3a)]$ |
| AAT | $2a[s^3L_1L_2 + s^2 L_2R_1 + sg(L_1 + L_2) + gR_1]$ | $[s^3L_1L_2 + s^2L_2(2a +R_1) + sg(L_1 +L_2) + g(2a +R_1)]$ |
| AAC | $2a[s^2L_2R_2 + sgL_2 + gR_2]$ | $[s^2L_2 (2a + R_2) + sgL_2 +g(2a + R_2)]$ |
| | | |
| AGA | $a(sL_1 + 2a)$ | $[(sL_1 + 3a)]$ |
| AGG | $[(s^2L_1^2 + 3saL_1 + 2a^2)]$ | $[(2sL_1 + 3a)]$ |

FIG. 8A Impedance expressions for the codon circuit model (serial - parallel version)

| Codon | Expression 1 | Expression 2 |
|---|---|---|
| AGT | $s^4 L_1^2 L_2 + s^3 L_1 L_2 (2a + R_1) + s^2 [L_2(2aR_1 + gL_1) + gL_1^2] + sg[L_1(2a + R_1) + 2aL_2] + 2agR_1$ | $\{2s^3 L_1 L_2 + s^2 L_2(R_1 + 2a) + sg(2L_1 + L_2) + g(R_1 + 2a)\}$ |
| AGC | $s^3 L_1 L_2 R_2 + s^2 L_2(2aR_2 + gL_1) + sg(2aL_2 + L_1 R_2) + 2agR_2$ | $[(s^3 L_1 L_2 + s^2 L_2(2a + R_2)] + sg(L_1 + L_2) + g(2a + R_2)]$ |
| ATA | $a[s^3 L_1 L_2 + s^2 L_2 (R_1 + a) + sg(L_1 + L_2) + g(R_1 + a)]$ | $[s^3 L_1 L_2 + s^2 L_2(R_1 + 2a) + sg(L_1 + L_2) + g(R_1 + 2a)]$ |
| ATG | $\{s^4 L_1 L_2^2 + s^3 L_1 L_2 (2a + R_1) + s^2 [a L_2 (a + R_1) + gL_1(L_1 + L_2)] + sg[L_1(2a + R_1) + aL_2)] + ag(R_1 + a)\}$ | $[2s^3 L_1 L_2 + s^2 L_2 (R_1 + 2a) + sg(2L_1 + L_2) + g(R_1 + 2a)]$ |
| ATT | $\{s^6 L_1^2 L_2^2 + s^5 L_1 L_2^2 (a + 2R_1) + s^4 L_2 [L_2 R_1(a + R_1) + 2g L_1(L_1 + L_2)] + s^3 gL_2[L_1(a + 3R_1) + L_2(a + 2R_1)] + s^2 g[2L_2 R_1(a + R_1) + g(L_1 + L_2)^2] + sg^2(a + 2R_1)(L_1 + L_2) + g^2 R_1(a + R_1)\}$ | $[2s^5 L_1 L_2^2 + s^4 L_2^2 (2R_1 + a) + 2s^3 gL_2(2L_1 + L_2) + 2s^2 gL_2(2R_1 + a) + 2sg^2(L_1 + L_2) + g^2(2R_1 + a)]$ |
| ATC | $s^5 R_2 L_1 L_2^2 + s^4 L_2^2 [R_2(R_1 + a) + gL_1)] + s^3 [L_2 R_2 g(L_1 + L_2) + g(L_2 L_2(R_1 + a) + R_2 L_1 L_2)] + s^2 [L_2 R_2 g(R_1 + a) + g(L_2 g(L_1 + L_2) + R_2 L_2 (R_1 + a))] + sg(L_2 g(R_1 + a) + R_2 g(L_1 + L_2)) + gR_2 g(R_1 + a)$ | $s^5 L_1 L_2^2 + s^4 L_2^2(a + 2R_1) + s^3 gL_2(2L_1 + 2L_2) + s^2 2gL_2(a + 2R_1) + sg^2(L_1 + 2L_2) + g^2(a + R_1 + R_2)$ |
| ACA | $a[s^2 L_2(a + R_2) + sgL_2 + g(a + R_2)]$ | $[s^2 L_2(2a + R_2) + sgL_2 + g(2a + R_2)]$ |
| ACG | $s^3 L_1 L_2(a + R_2) + s^2 L_2[gL_1 + a(a + R_2)] + sg[L_1(a + R_2) + aL_2] + ag(a + R_2)$ | $[s^3 L_1 L_2 + s^2 L_2(2a + R_2) + sg(L_1 + L_2) + g(2a + R_2)]$ |

FIG. 8B Impedance expressions for the codon circuit model
(serial - parallel version)

| | | |
|---|---|---|
| ACT | $s^5 L_2L_1 L_2(a + R_2) + s^4 [L_2 (L_1 gL_2 + R_1 L_2(a + R_2)) + g(L_1 + L_2)] + s^3 [L_2 R_1 gL_2 + g(L_1 +L_2) L_2(a + R_2)] + s^2 [L_2 R_1 g(a + R_2) + g(R_1 L_2(a + R_2) + (L_1 + L_2) gL_2)] + sg[R_1 gL_2 + (L_1 + L_2) g(a + R_2)] + gR_1 g(a + R_2)$ | $s^5 L_1 L_2{}^2 + s^4 L_2{}^2(a + R_1 + R_2) + 2s^3 gL_2(L_1 + L_2) + 2s^2 gL_2(a + R_1 + R_2) + sg^2(L_1 + 2L_2) + g^2(a + R_1 + R_2)$ |
| ACC | $s^4 L_2(a + R_2) L_2R_2 + s^3 [gL_2L_2R_2 + L_2(a + R_2) gL_2] + s^2 [g(a + R_2)L_2R_2 + gL_2gL_2 + L_2(a + R_2) gR_2] + s [g(a + R_2)gL_2 + gL_2gR_2] + g(a + R_2)gR_2$ | $s^4 L_2{}^2(a + 2R_2) + 2s^3 gL_2{}^2 + 2s^2 gL_2(a + 2R_2) + 2sg^2 L_2 + g^2(a + 2R_2)$ |
| GAA | same as AGA | same as AGA |
| GAG | same as AGG | same as AGG |
| GAT | same as AGT | same as AGT |
| GAC | same as AGC | same as AGC |
| GGA | $2a(sL_1 + a)$ | $[(2sL_1 + 3a)]$ |
| GGG | $2(sL_1 + a)$ | 3 |
| GGT | $2s^4 L_1{}^2 L_2 + 2s^3 L_1 L_2(a + R_1) +2s^2[L_2(aR_1 + gL_1) + gL_1{}^2] +2sg[L_1(a +R_1)+ aL_2] + 2agR_1$ | $[3s^3 L_1 L_2 + s^2 L_2(2a + R_1) + sg(3L_1 + L_2) + g(2a + R_1)]$ |
| GGC | $2[s^3 L_1L_2R_2 + s^2 L_2(aR_2 + gL_1) + sg(aL_2 + L_1R_2) + agR_2]$ | $[2s^3 L_1 L_2 + s^2 L_2(2a + R_2) + sg(2L_1 + L_2) + g(2a + R_2)]$ |
| GTA | $a[2s^3 L_1 L_2 + s^2 L_2(R_1 + a) + sg(2L_1 + L_2) + g(a+R_1)]$ | $[2s^3 L_1 L_2 + s^2 L_2(R_1 + 2a) + sg(2L_1 + L_2) + g(2a+R_1)]$ |
| GTG | $2s^4 L_1{}^2 L_2 + s^3 L_1 L_2(3a + R_1) + s^2[aL_2(a + R_1) + gL_2(2L_1 + L_2)] + sg[L_1(3a + R_1 + R_2) + aL_2] + ag(a + R_1)$ | $[3s^3 L_1 L_2 + s^2 L_2(R_1 + 2a) + sg(3L_1 + L_2) + g(2a+R_1)]$ |

FIG. 8C Impedance expressions for the codon circuit model (serial - parallel version)

| | | |
|---|---|---|
| GTT | $2s^6L_1^2L_2^2 + s^5L_1L_2^2(a + 2R_1) + s^4L_2[L_2R_1(a + R_1) + gL_1(4L_1 + 3L_2)] + s^3gL_2[L1(a + 5R_1) + L2(a + 2R_1)] + s^2g[2L_2R_1(a + R_1) + g(2L_1 + L_2)(L_1 + L_2)] + sg^2[L_1(a + 3R_1) + L2(a + 2R_1)] + g^2R_1(a + R_1)$ | $3s^5L^2L_2^2 + s^4L_2^2(a + 2R_1) + 2s^3gL_2(3L_1 + L_2) + 2s^2gL_2(a + 2R_1) + sg^2(3L_1 + 2L_2) + g^2(a + 2R_1)$ |
| GTC | $2s^5R_2 L_1L_2^2 + s^4 L_2^2 [R_2(R_1+ a) + 2g L_1] + s^3 [L_2 R_2 g(L_1+L_2) + g(L_2 L_2 (R_1+ a) + 2R_2 L_2)] + s^2 [L_2 R_2 g(R_1+ a) + g(L_2 g(L_1+L_2) + R_2L_2 (R_1+ a))] + sg(L_2g(R_1+ a) + R_2 g(L_1+L_2)) + g^2R_2 (R_1+ a)$ | $2 s^5L_1L_2^2 + s^4L_2^2(a + R2 +R_1) + s^3gL_2(4L_1 + 2L_2) + 2s^2gL_2(a + R2 + R_1) + sg^2(2L_1 +2 L_2) + g^2(a + 2R_1)$ |
| GCA | $a[s^3L_1L_2 + s^2 L_2(R_2 + a) + sg(L_1 + L_2) + g(a + R_2)]$ | $[s_3L_1L_2 + s^2 L_2(R_2 + 2a) + sg(L_1 + L_2) + g(2a + R_2)]$ |
| GCG | $s^4L_1^2L_2 + s^3L_1L_2(2a + R_2) + s^2[aL_2(a + R_2) + gL_2(L_1 + L_2)] + sg[L_1(2a + R_2) + aL_2] + ag(a + R_2)$ | $[2s^3L_1L_2+s^2L_2(R_2+2a)+sg(2L_1+L_2)+g(2a+R_2)]$ |
| GCT | $\{s^6 L_1^2 L_2^2 + s^5 L_1 L_2^2(a + R_1 + R_2) + s^4 L_2 [L_2R_1(a + R_2) + 2g L_1(L_1 + L_2 )] + s^3 gL_2[L_1(a + 2R_1 + R_2) + L_2(a + R_1 + R_2)] + s^2g[2L_2R_1(a + R_2) + g(L_1 + L_2)^2] + sg^2(a + R_1 + R_2)(L_1 + L_2) + g^2R_1 (a + R_2)\}$ | $2s^5L_1L_2^2 + s^4L_2^2(a + R_1 + R_2) + 2s^3gL_2(2L_1 + L_2) + 2s^2gL_2(a + R_1 + R_2) + 2sg^2(L_1 + L_2) + g^2(a + R_1 + R_2)$ |

FIG. 8D Impedance expressions for the codon circuit model
(serial – parallel version)

| | | |
|---|---|---|
| GCC | $s^5L_2 L_1L_2^2 + s^4 L_2^2 [R_2 (R_1+ a) + gL_1] + s^3 [L_2 R_2 g(L_1+L_2) + g(L_2 L_2 (R_1+ a) + R_2 L_1L_2)] + s^2 [L_2 R_2 g(R_1+ a) + g(L_2 g(L_1+L_2) + R_2 L_2 (R_1+ a))] + sg(L_2g(R_1+ a) + R_2 g(L_1+L_2)) + gR_2 g(R_1+ a)$ | $s^5L_1L_2^2 + s^4L_2^2(a + 2R_2) + s^3gL_2(2L_1 +2L_2) + 2s^2gL_2(a + 2R_2) + sg^2(L_1 + 2L_2) + g^2(a + 2R_2)$ |
| TAA | same as ATA | same as ATA |
| TAG | same as ATG | same as ATG |
| TAT | same as ATT | same as ATT |
| TAC | same as ATC | same as ATC |
| TGA | same as GTA | same as GTA |
| TGG | same as GTG | same as GTG |
| TGT | same as GTT | same as GTT |
| TGC | same as GTC | same as GTC |
| TTA | $2a[s^3 L_1L_2+ s^2 L_2R_1+ sg(L_1+L_2) + gR_1]$ | $[2s^3L_1L_2+s^2L_2(a +2R_1) +2sg(L_1+L_2) + (a+2R_1)]$ |
| TTG | $2s^4L_1^2L_2 + 2s^3L_1L_2(a + R_1) + 2s^2[aL_2R_1 + gL_2(L_1 + L_2)] + 2sg[L_1(a + R_1) + aL_2] + 2agR_1$ | $[3s^3L_1L_2+s^2 L_2(a +2R_1) +sg(L_1+L_2) + g(a +2R_1)]$ |
| TTT | $2[s^3 L_1L_2+ s^2L_2R_1+sg(L_1+L_2)+gR_1]$ | $3(s^2L_2 + g)$ |
| TTC | $s^5L_2 L_1L_2^2 + s^4 L_2^2 [R_2 R_1 + gL_1] + s^3 [L_2 R_2 g(L_1+L_2) + g(L_2 L_2R_1 + R_2 L_1L_2)] + s^2 [L_2 R_2 g(R_1+ a) + g(L_2 g(L_1+L_2) + R_2 L_2R_1)] + sg(L_2g(R_1+ a) + R_2 g(L_1+L_2)) + gR_2 g(R_1+ a)$ | $2 s^5L_1L_2^2 + 2s^4L_2^2R_1 + s^3gL_2(4L_1 + 3L_2) + 2s^2gL_2(2R_1 + R2) + sg^2(2L_1 + 3L_2) + 2g^2(2R1 + R_1)$ |
| TCA | $a[s^3L_1L_2 + s^2L_2(R_1 + R_2) + sg(L_1+2L_2) + g(R_1+R_2)]$ | $[s^3L_1L_2 + s^2L_2(a + R1 + R_2) + sg(L_1+2L_2) + g(a + R_1+R_2)]$ |

FIG. 8E Impedance expressions for the codon circuit model
(serial - parallel version)

| | | |
|---|---|---|
| TCG | $s^4 L_1^2 L_2 + s^3 L_1 L_2 (a + R_1 + R_2) + s^2 [a L_2 (R_1 + R_2) + g L_2 (L_1 + 2L_2)] + sg[L_1 (a + R_1 + R_2) + 2aL_2] + ag(R_1 + R_2)$ | $[2s^3 L_1 L_2 + s^2 L_2 (a + R_1 + R_2) + 2sg(L_1 + L_2) + g(a + R_1 + R_2)]$ |
| TCT | $s^6 L_1^2 L_2^2 + s^5 L_1 L_2^2 (2R_1 + R_2) + s^4 L_2 [L_2 R_1 (R_1 + R_2) + g L_1 (2L_1 + 3L_2)] + s^3 g L_2 (3R_1 + R_2)(L_1 + L_2) + s^2 g [2L_2 R_1 (R_1 + R_2) + g(L_1 + L_2)(L_1 + 2L_2)] + sg^2 R_1 (2L_1 + 3L_2) + g^2 R_1^2$ | $2s^5 L_1^2 L_2 + s^4 L_2^2 (2R_1 + R_2) + s^3 g L_2 (4L_1 + 3L_2) + 2s^2 g L_2 (2R_1 + R_2) + sg^2 (2L_1 + 3L_2) + g^2 (2R_1 + R_2)$ |
| TCC | $s^5 L_2 \, L_1 L_2^2 + s^4 \, L_2^2 \, [R_2 R_1 + g L_1] + s^3 \, [L_2 R_2 g(L_1+L_2) + g(L_2 L_2 R_1 + R_2 L_1 L_2)] + s^2 \, [L_2 R_2 g(R_1+ a) + g(L_2 g(L_1+L_2) + R_2 L_2 R_1)] + sg(L_2 g(R_1+ a) + R_2 g(L_1+L_2)) + g R_2 g(R_1+ a)$ | $s^5 L_1 L_2^2 + s^4 L_2^2 (R_1 + 2R_2) + s^3 g L_2 (2L_1 + 3L_2) + 2s^2 g L_2 (R_1 + 2R_2) + sg^2 (L_1 + 3L_2) + g^2 (R_1 + 2R_2)$ |
| CAA | same as ACA | same as ACA |
| CAG | same as ACG | same as ACG |
| CAT | same as ACT | same as ACT |
| CAC | same as ACC | same as ACC |
| CGA | same as GCA | same as GCA |
| CGG | same as GCG | same as GCG |
| CGT | same as GCT | same as GCT |
| CGC | same as GCC | same as GCC |
| CTA | same as TCA | same as TCA |
| CTG | same as TCG | same as TCG |
| CTT | same as TCT | same as TCT |
| CTC | same as TCC | same as TCC |
| CCA | $2a(s^2 L_2 R_2 + g L_2 s + g R_2)$ | $[2s^2 L_2 (a + 2R_2) + g L_2 s + g(a + 2R_2)]$ |
| CCG | $2[s^3 L_1 L_2 R_2 + s^2 L_2 (aR_2 + g L_1) + sg(aL_2 + L_1 R_2) + agR_2]$ | $[s^3 L_1 L_2 + s^2 a L_2 (a+2R_2) + sg(2L_2 + L_1) + g(a+2R_2)]$ |

FIG. 8F Impedance expressions for the codon circuit model (serial - parallel version)

| CCT | $s^5 L_2 R_2 L_1 L_2 + s^4 L_2 (R_2 L_2 R_1 + g L_1 L_2) + s^3 [L_2 R_2 g(L_1 + L_2) + g(L_2 L_2 R_1 + R_2 L_1 L_2)] + s^2 [L_2 R_2 g R_1 + g(L_2 g(L_1 + L_2) + R_2 L_2 R_1)] + sg[L_2 g R_1 + R_2 g(L_1 + L_2)] + g R_2 g R_1$ | $s^5 L_1^2 L_2 + s^4 L_2^2 (R_1 + 2R_2) + 2s^3 g L_2 (L_1 + L_2) + 2s^2 g L_2 (R_1 + 2R_2) + sg^2 (L_1 + 2L_2) + g^2 (R_1 + 2R_2)$ |
|---|---|---|
| CCC | $2(s^2 L_2 R_2 + s L_2 g + R_2 g) / [3(s^2 L_2 + g)]$ | $3(s^2 L_2 R_2 + s L_2 g + R_2 g) / [2(s^2 L_2 + g)]$ |

FIG. 8G Impedance expressions for the codon circuit model
(serial - parallel version)

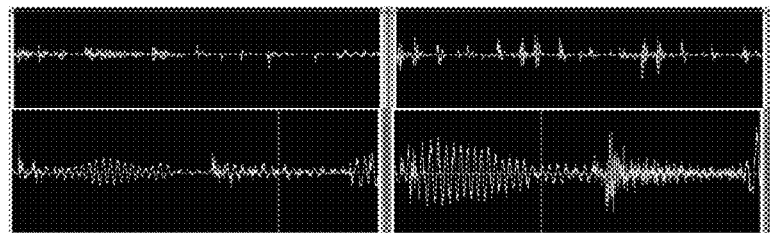
FIG. 9 Example of two user-specified input sound files and the corresponding system generated output sound files
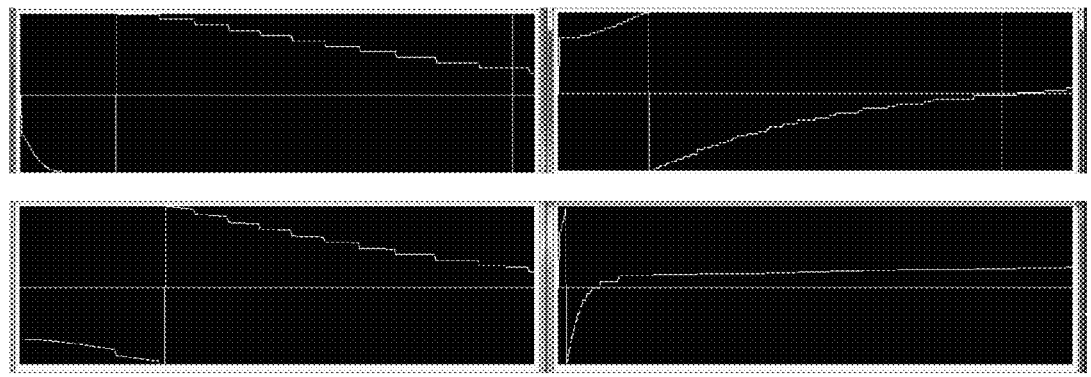
FIG. 10 The four nucleotide sound waves generated by the nucleotide circuit model for the default sinusoidal wave input

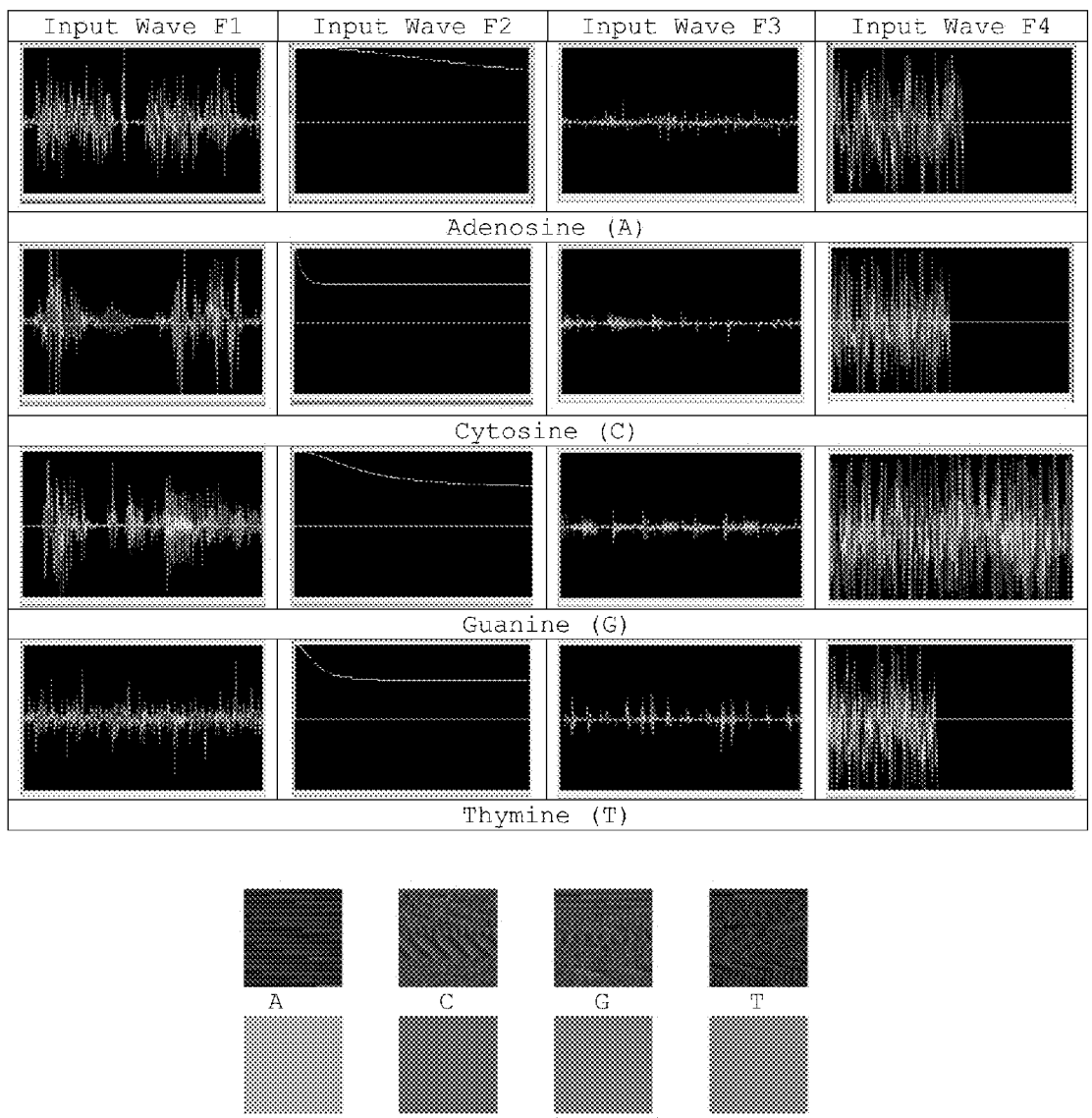
FIG. 11 Wave, texture and signature image output for the four nucleotides

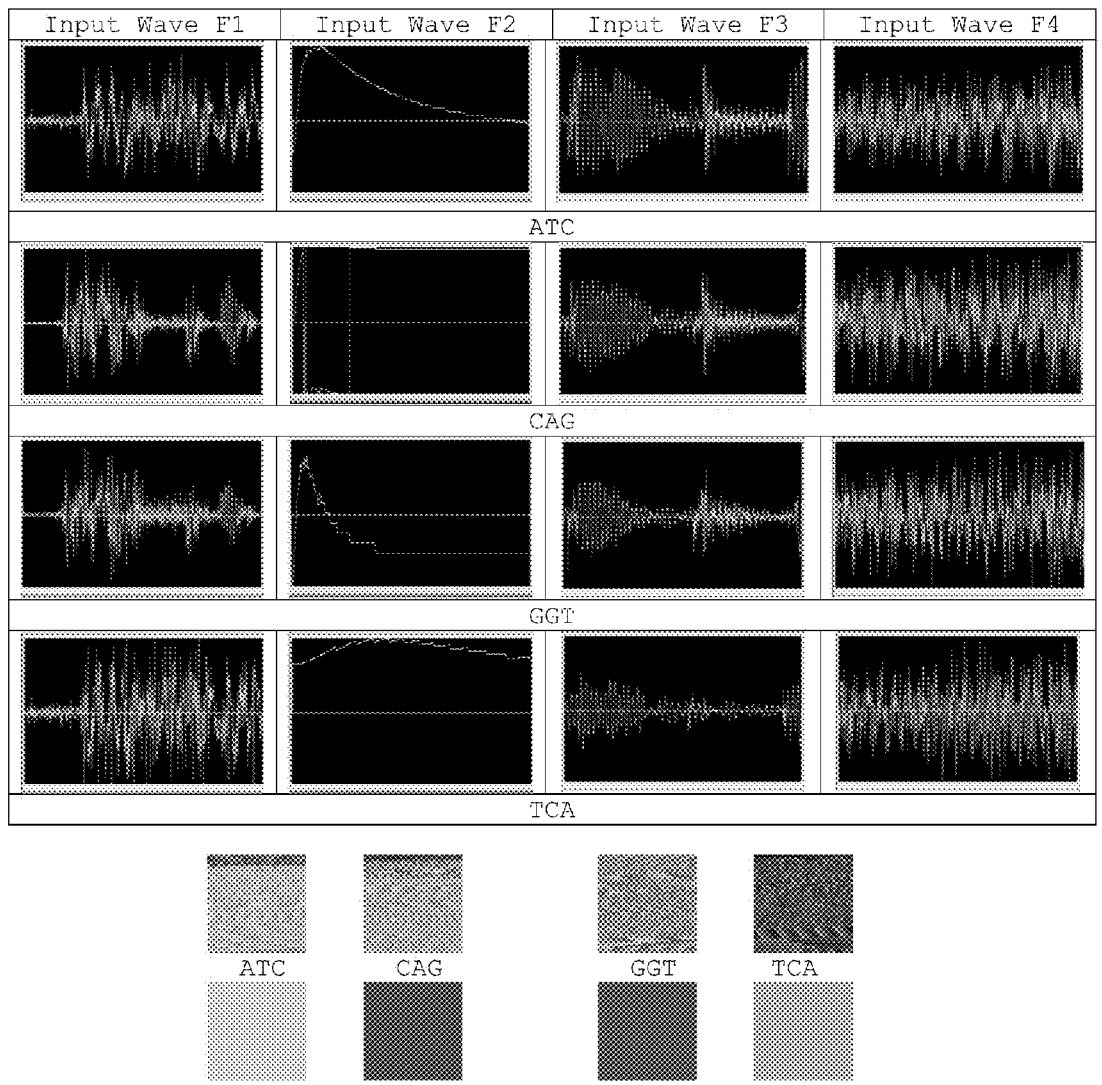
FIG. 12 Examples of wave, texture and signature image output for select codons

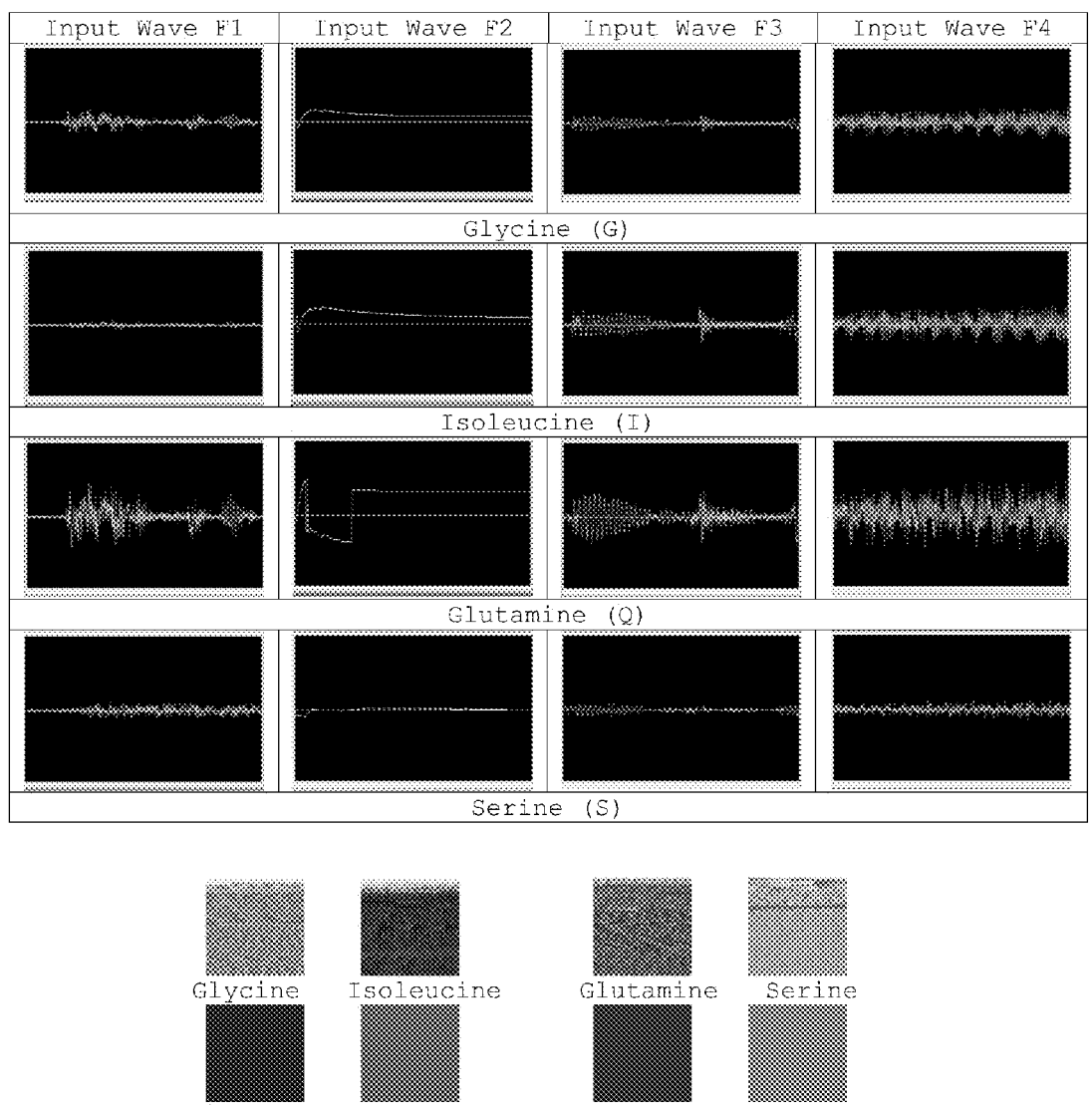
FIG. 13 Examples of wave, texture and signature image output for select amino acids

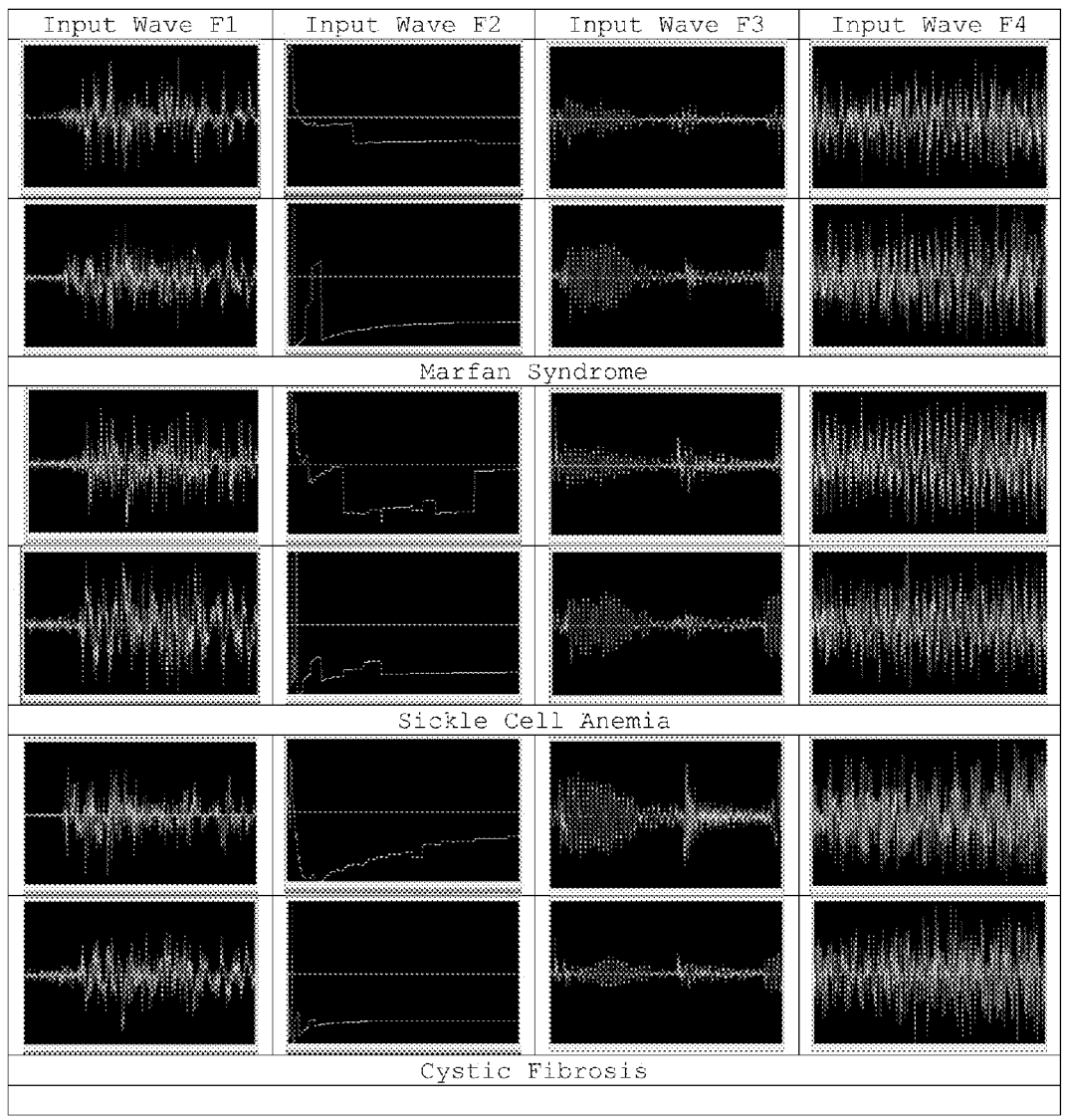
FIG. 14 Wave output for select diseases - amino acid and DNA versions (top and bottom rows, respectively)

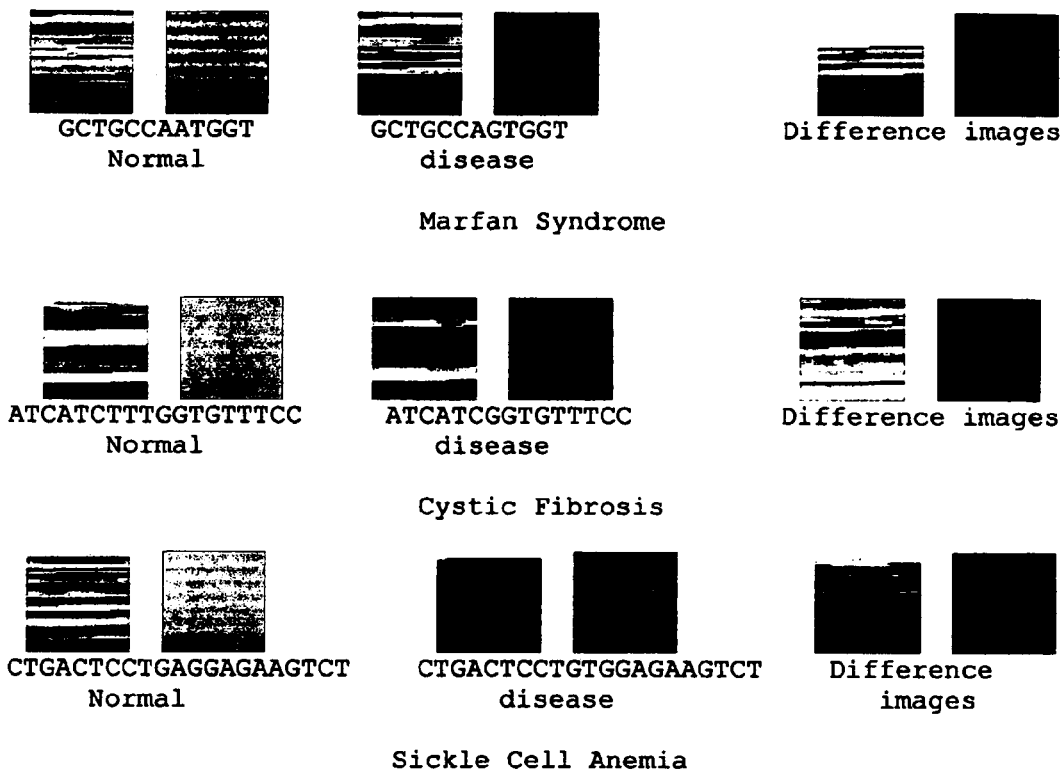
FIG 15. Texture, difference and signature images for select diseases (DNA version)
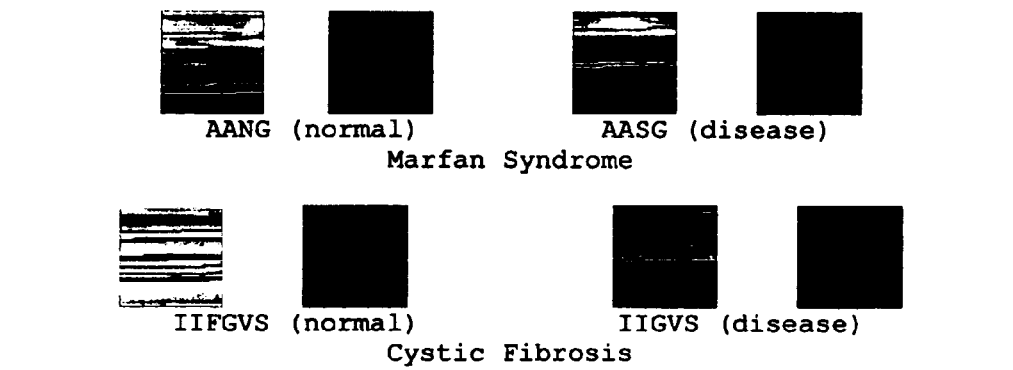
FIG 16A. Texture, difference and signature images for select diseases (amino acid version)

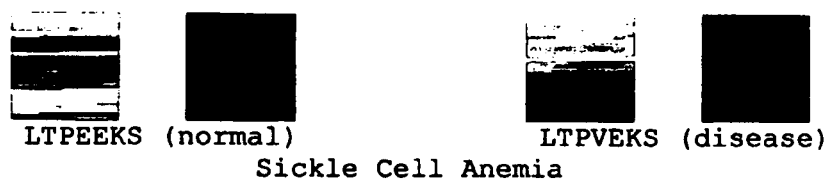
LTPEEKS (normal)   LTPVEKS (disease)
Sickle Cell Anemia
FIG 16B. Texture, difference and signature images for select diseases (amino acid version)
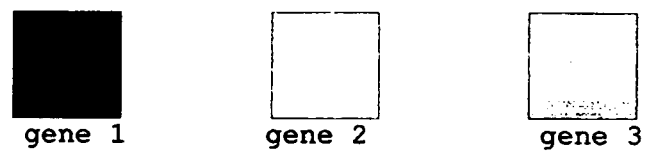
gene 1   gene 2   gene 3
FIG 17. Signatures of Cataract Genes Fingerprint input
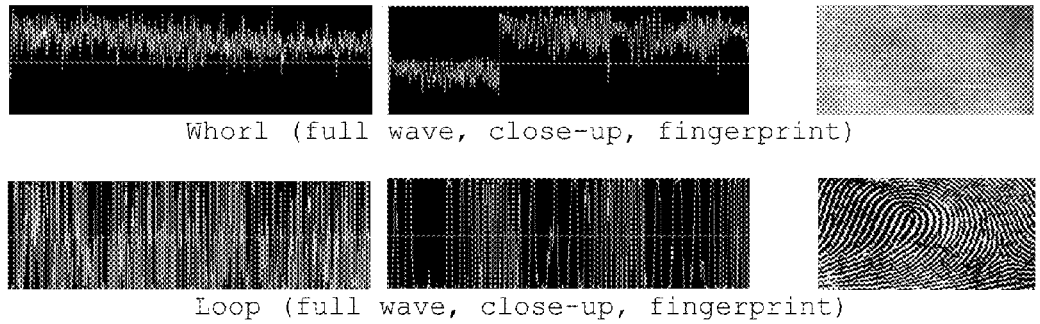
FIG. 18 Examples of fingerprint conversion into waves
Speech input
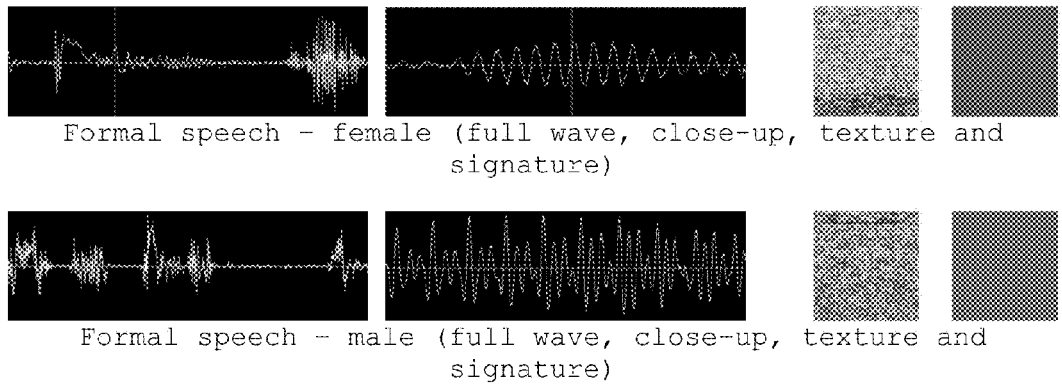
FIG. 19 Examples of human speech converted to images
Retinal Scan input
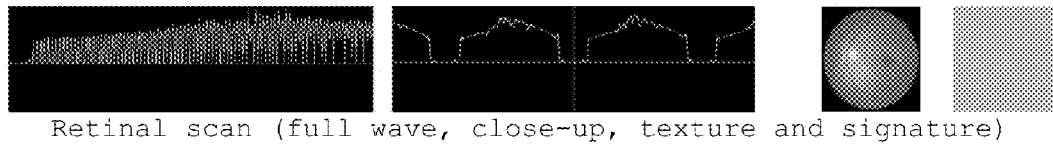
Retinal scan (full wave, close-up, texture and signature)
FIG. 20 Example of retinal image conversion into waves and associated signature

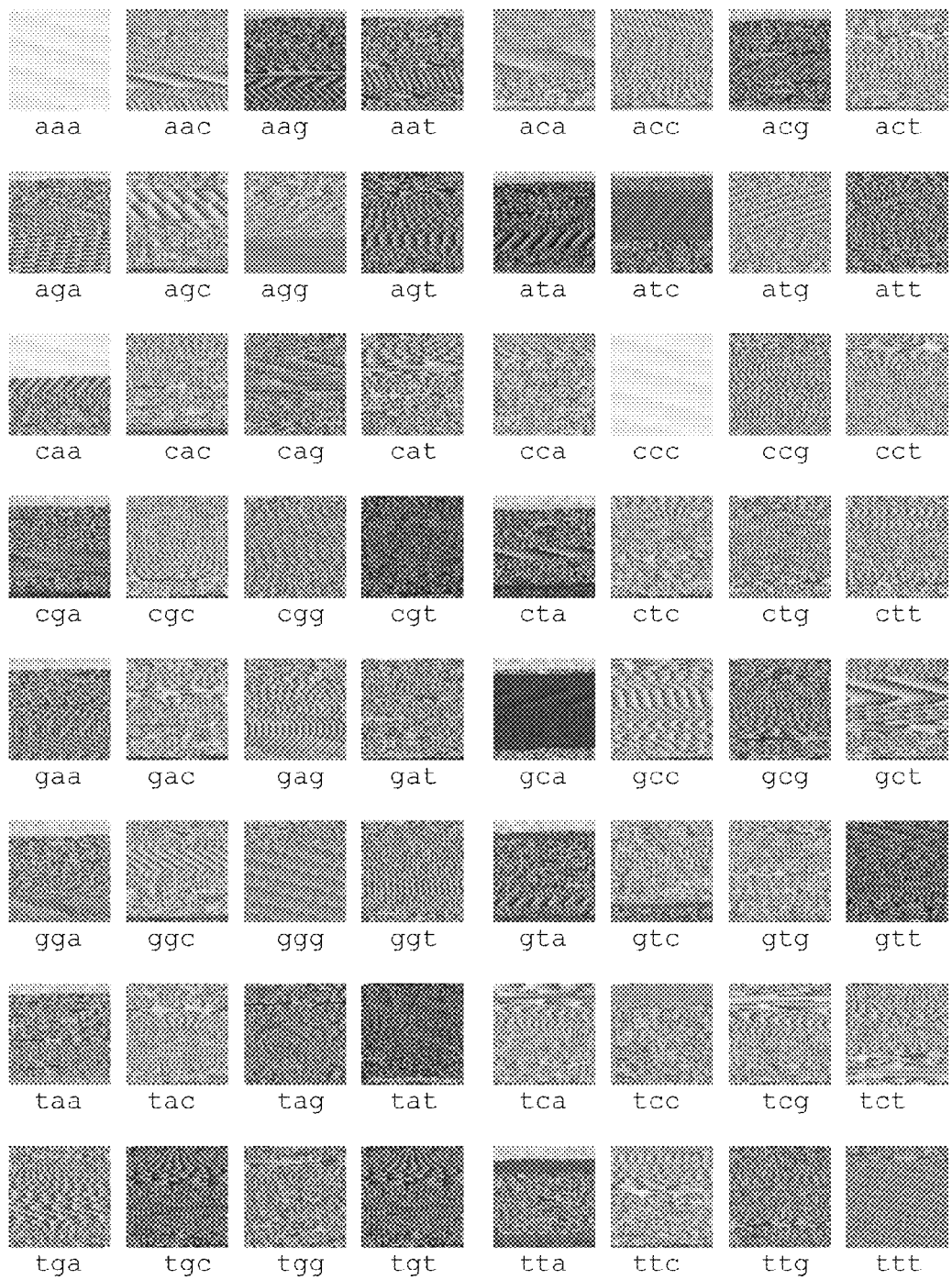
FIG. 21 Textured images produced by the OMNIGENE system for all 64 codons using a parallel-serial RLC circuit implementation with sinusoidal wave input

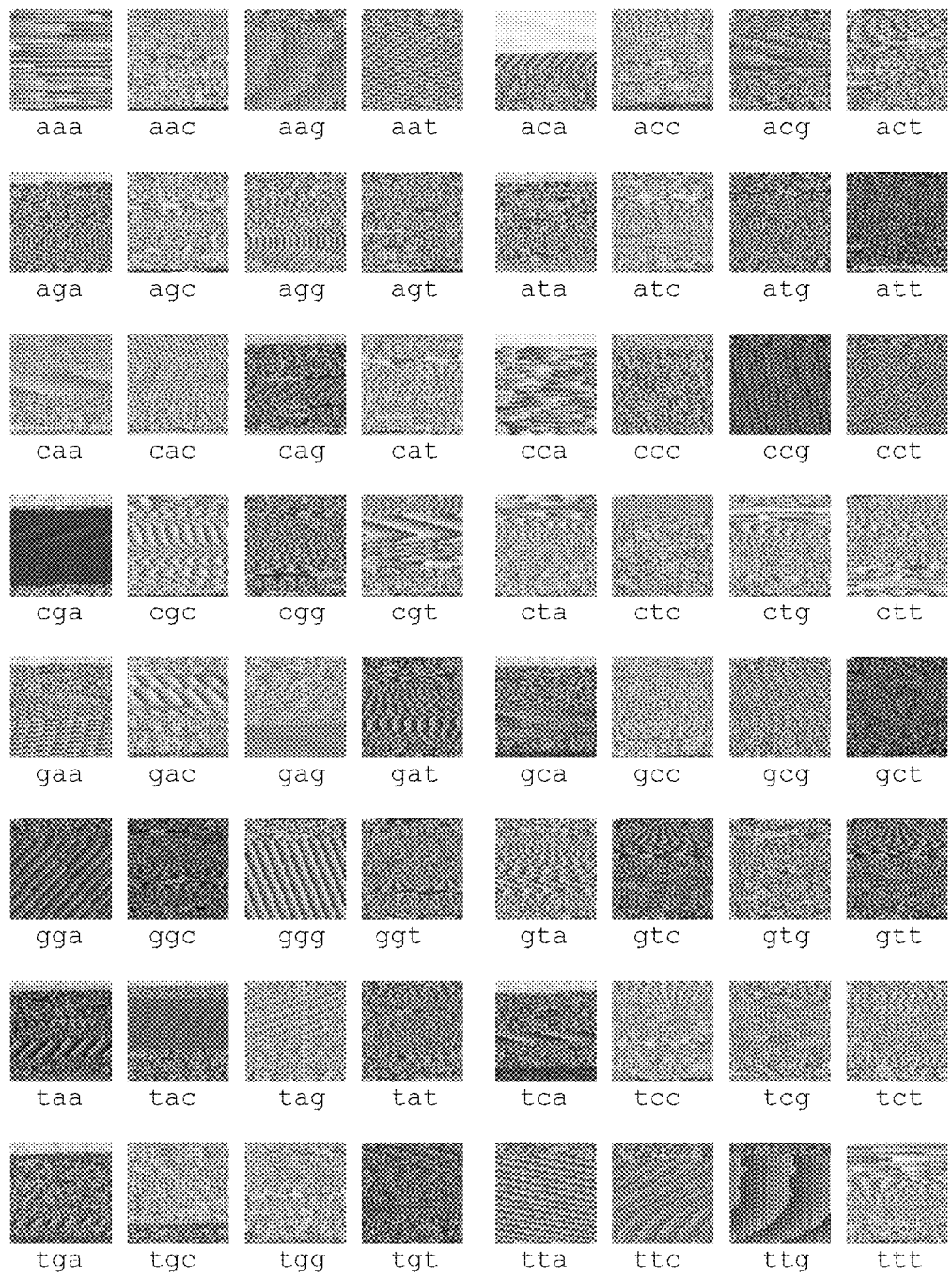
FIG. 22 Textured images produced by the OMNIGENE system for all 64 codons using a serial - parallel RLC circuit implementation with sinusoidal wave input

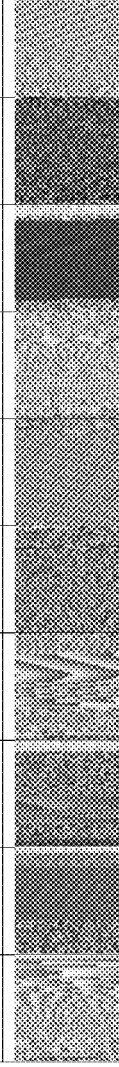
FIG. 23 Textured images produced by the system for Codon + one other input type (speech or fingerprint or retinal scan)

| circuit | codon | Speech + fingerprint wave input | | | |
|---|---|---|---|---|---|
| | | Male + loop | Female + loop | Male + whorl | Female + whorl |
| Parallel/ Serial | atg |  |  |  | 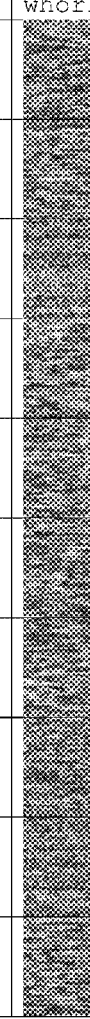 |
| | cgt |  |  |  | 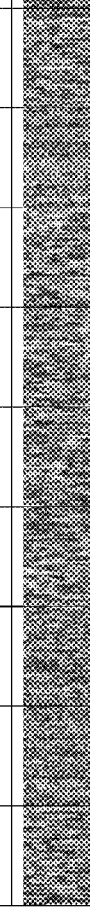 |
| | gca | 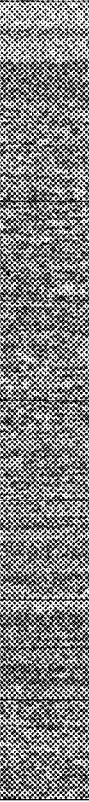 | 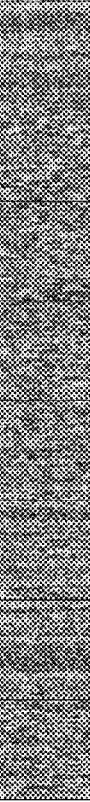 | 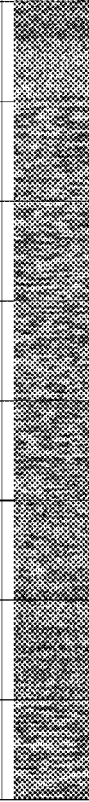 | 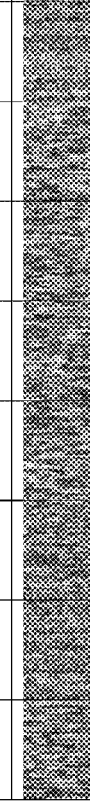 |
| | tac |  |  |  | 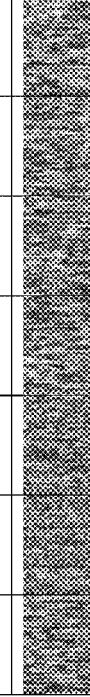 |
| | ttt |  |  |  | 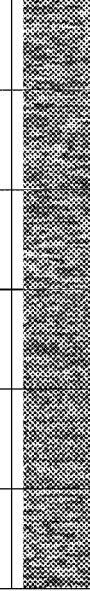 |
| Serial/ Parallel | atg |  | 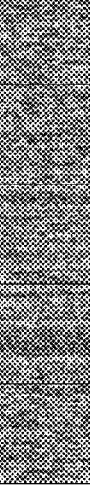 |  | 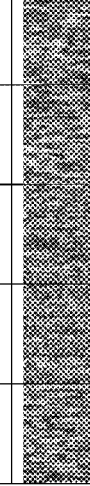 |
| | cgt |  | 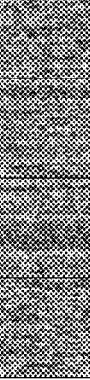 |  | 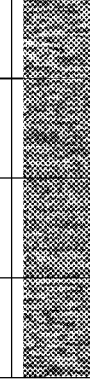 |
| | gca | 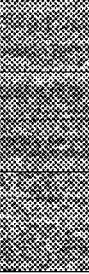 | 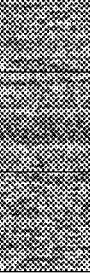 |  | 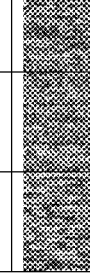 |
| | tac | 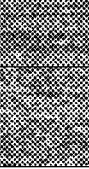 |  |  | 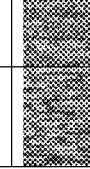 |
| | ttt |  |  |  |  |
FIG. 24 Textured images produced by the system for Codon + two other input types (male or female speech + loop or whorl fingerprint)

| circuit | codon | Speech + fingerprint + retinal scan wave input ||||
| --- | --- | --- | --- | --- | --- |
| | | Male + loop + retina | Female + loop + retina | Male + whorl + retina | Female + whorl + retina |
| Parallel/ Serial | atg | 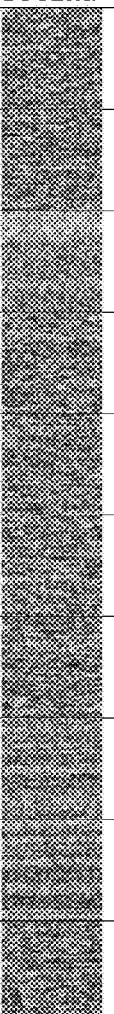 | 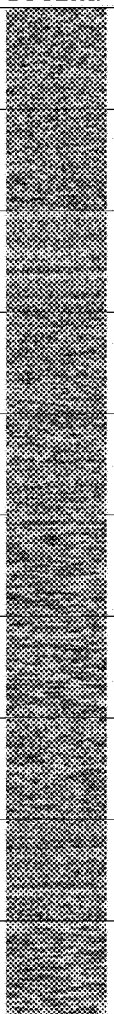 |  | 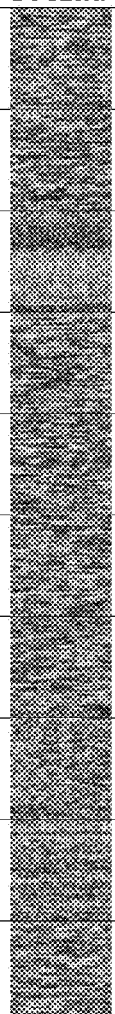 |
| | cgt | 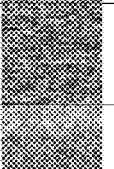 | 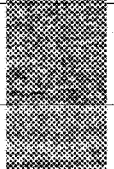 |  | 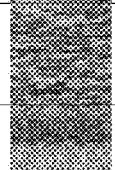 |
| | gca | 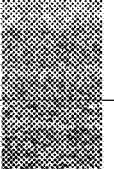 | 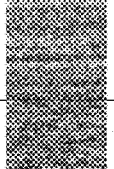 |  |  |
| | tac | 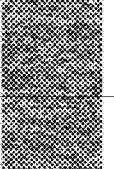 | 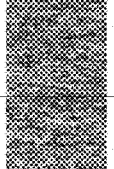 |  | 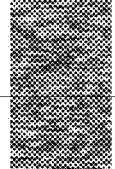 |
| | ttt | 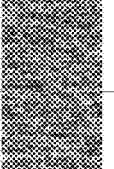 | 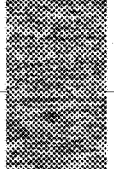 |  | 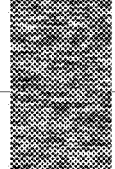 |
| Serial/ Parallel | atg | 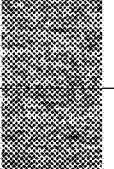 | 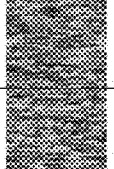 |  | 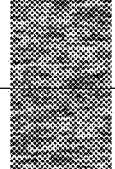 |
| | cgt | 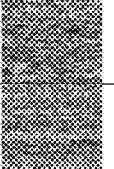 | 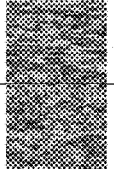 |  | 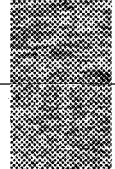 |
| | gca | 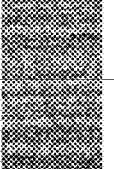 | 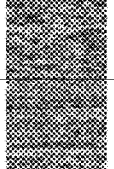 |  | 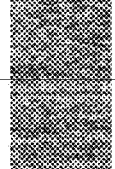 |
| | tac | 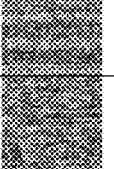 | 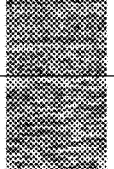 |  | 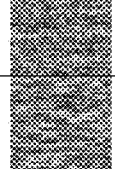 |
| | ttt | 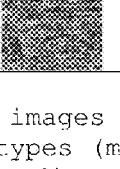 | 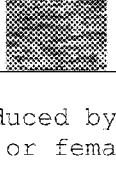 | 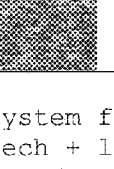 | 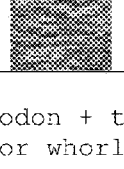 |
FIG. 25 Textured images produced by the system for Codon + three other input types (male or female speech + loop or whorl fingerprint + retinal scan)

| circuit | codon | Speech + retinal scan input | | Fingerprint + retinal scan wave input | |
|---|---|---|---|---|---|
| | | Male + retina | Female + retina | Loop + retina | whorl + retina |
| Parallel/ Serial | atg |  |  | 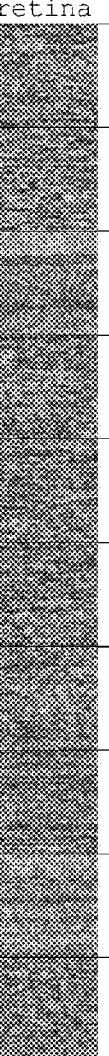 |  |
| | cgt | 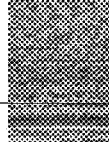 | 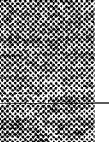 |  |  |
| | gca |  |  | 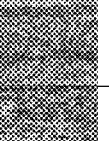 |  |
| | tac |  | 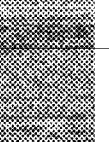 |  |  |
| | ttt |  |  |  |  |
| Serial/ Parallel | atg |  |  | 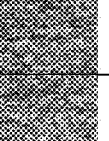 |  |
| | cgt |  | 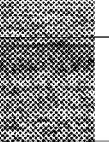 | 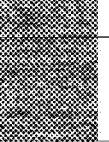 | 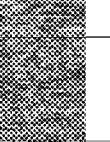 |
| | gca |  |  |  |  |
| | tac | 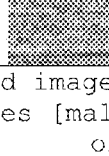 | 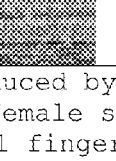 | 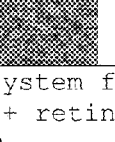 | 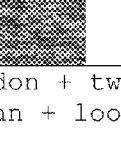 |
| | ttt |  |  |  |  |
FIG. 26 Textured images produced by the system for Codon + two other input types [male or female speech + retinal scan + loop or whorl fingerprint)

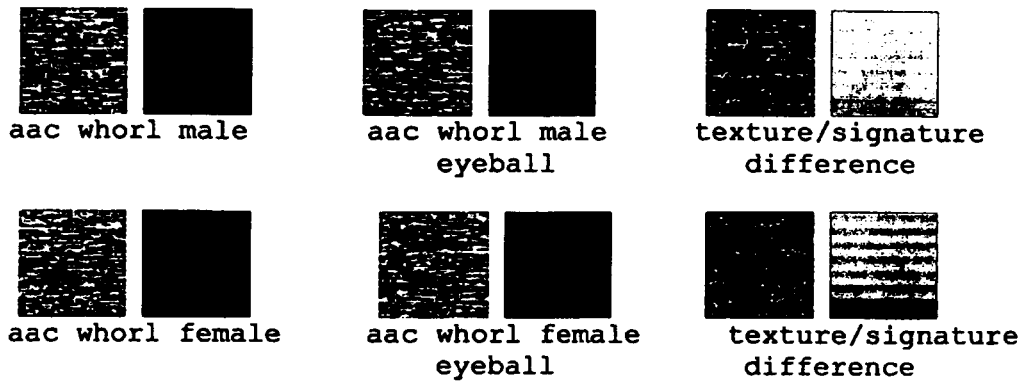
FIG. 27 Comparative system responses to four input types [AAC codon + retinal scan + whorl fingerprint + speech (male/female)]
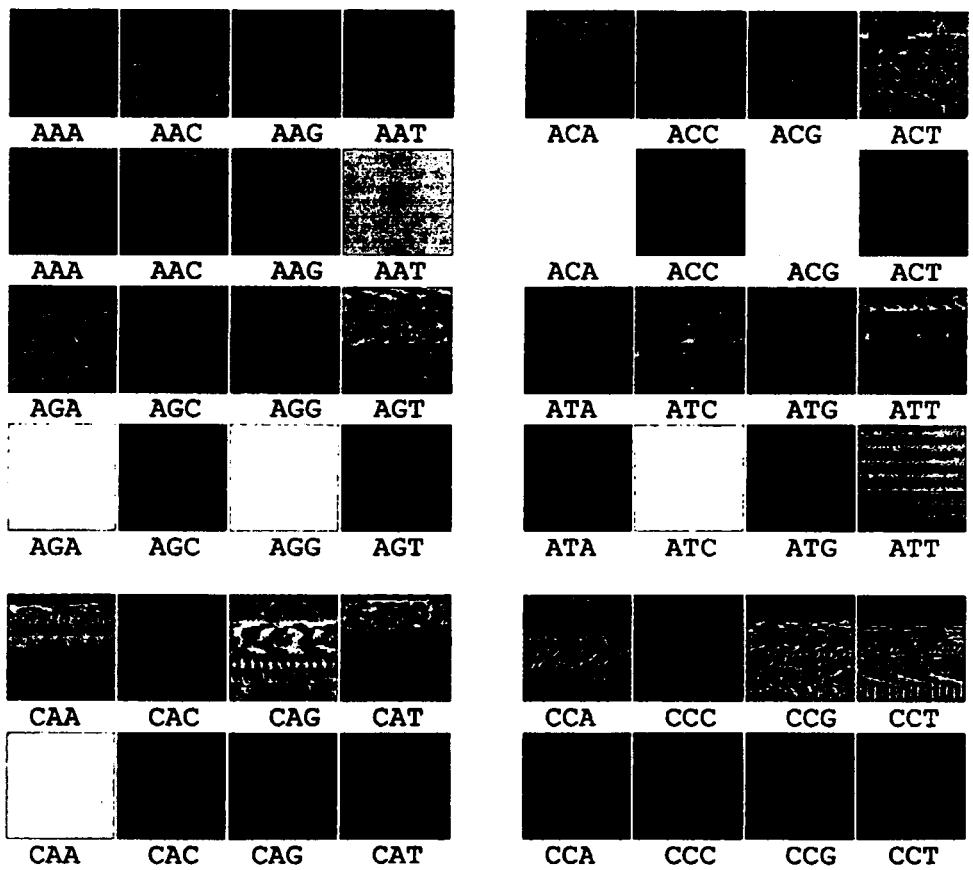
FIG. 28A Distinct texture patterns and signature images produced by OMNIGENE based on the first 32 codons

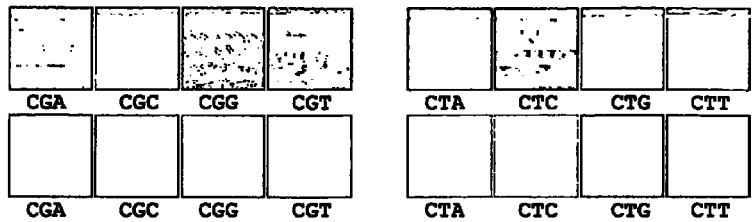
FIG. 28B Distinct texture patterns and signature images produced by OMNIGENE based on the first 32 codons
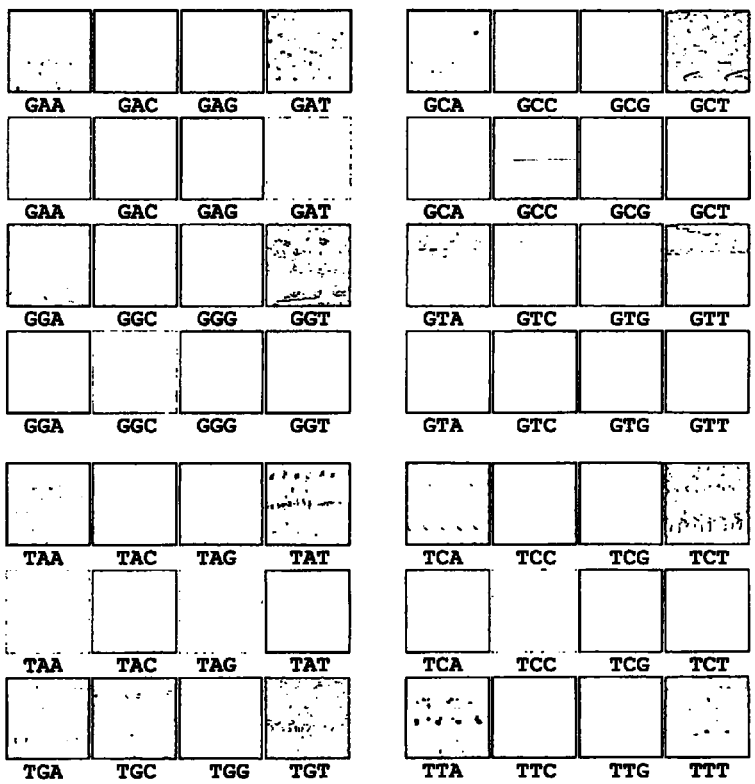
FIG. 29A Distinct texture patterns and signature images produced by OMNIGENE based on the second 32 codons

FIG. 29B Distinct texture patterns and signature images produced by OMNIGENE based on the second 32 codons
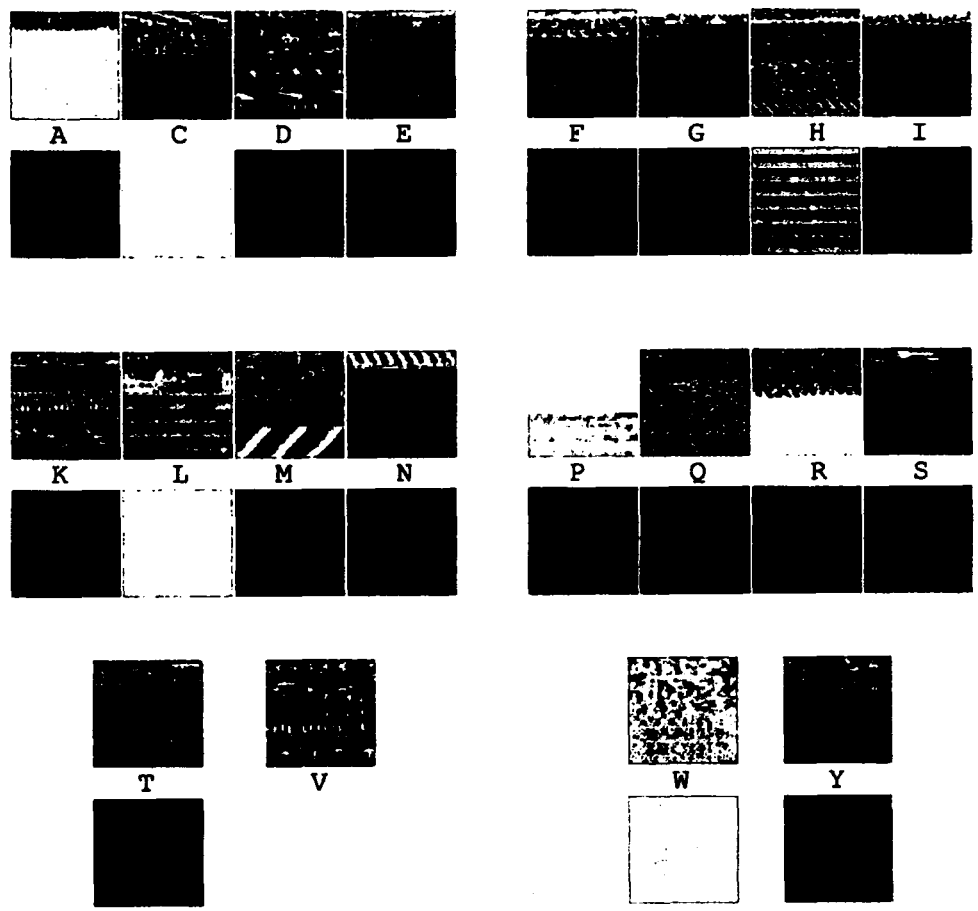
FIG. 30 Distinct texture patterns and signature images produced by OMNIGENE based on the 20·amino acids

OMNIGENE SOFTWARE SYSTEM

A portion of the disclosure of this patent document contains material which is subject to (copyright or mask work) protection. The (copyright or mask work) owner has no objection to the facsimile reproduction by anyone of the patent document or the patent disclosure, as it appears in the Patent and Trademark Office patent file, or records, but otherwise reserves all (copyright or mask work) rights whatsoever.

CROSS-REFERENCE TO RELATED APPLICATIONS

The inventor submitted a provisional application for patent (PTO/SB/16) titled "The OMNIGENE Software System with applications in. Biometric Identification, Medical and Pharmaceutical Research, Computer Security and the Design and Manufacture of Certain Household Products" to the US Patent Office on May 4, 2012 along with a filing fee of $125.00. The application contains a 2 page specification and 17 drawing sheets.

REFERENCE TO TABLE OR COMPUTER PROGRAM LISTING

The specification is accompanied by one PDF file containing three sets of drawings and one set of tables/mathematical formulae, and one TEXT file containing a computer program listing. The names of these two files are as follows:
a) OMNIGENE_DRAWINGS.PDF
b) OMNIGENE_Computer_Program.TXT

BACKGROUND OF THE INVENTION

The genetic makeup or DNA of an individual is usually described by a long string of molecules called nucleotides. These nucleotides which are four, in number are adenosine, cytosine, guanine and thymine represented by the symbols A, C, G and T. (U in the case of RNA), respectively. The genetic code of any organism is represented by a set of 64 codons. A codon is any combination of three nucleotides drawn from the four-nucleotide symbol set. These codons code for a set of 20 amino acids and each amino acid is represented by one or more codons. These amino acids are symbolically represented by the set {A, C, D, E, F, G, H, I, K, L, M, N, P, Q, R, S, T, V, W, Y} is A gene or a protein is a string of amino acids and the length of the string varies, depending on the protein or gene. Consequently, the genetic description of an individual can be specified at the symbolic level by a string of nucleotides drawn from the set {A, C, T (or U), G} or by a string of amino acids drawn from the set {A, C, D, E, F, G, H, I, K, L, M, N, P, Q, R, S, T, V, W, Y}.

Given that a molecule is nothing more than an ensemble of atoms configured in a particular manner and given that atoms vibrate, we can associate a single frequency or a set of frequencies to a molecule. In this work, we associate a set of frequencies with the nucleotides. The frequencies are drawn from the user's highly individualistic speech samples. Combining the nucleotides to produce a specific codon implies combining the frequencies of the underlying nucleotides in a prescribed manner to produce a unique set of frequencies for that codon. This procedure results in a characteristic set of frequencies being associated with each of the 64 codons. This, in turn, implies each amino acid can now be associated with another specific, but different, set of frequencies because the genetic code is a redundant code and all but two amino acids have more than one codon representing them. Consequently, when the user inputs a set of and an amino acid or DNA or RNA string, a unique wave pattern can be produced. This wave pattern can then converted into a unique visual pattern representing a composition of colors.

BRIEF SUMMARY OF THE INVENTION

The software system OMNIGENE has been developed which can, based on a user's unique speech patterns, fingerprints, retinal scan and DNA sample, generate a set of highly personalized and necessarily, unique texture and color patterns (hereinafter called the 'signature') which can be employed by the user in a variety of application areas including medical and pharmaceutical research, biometrics, computer security, fabric, clothing and upholstery design/manufacture. The biometric samples provided by the user are input into a special pair of electrical circuits in order to generate the unique color patterns. Over the lifetime of an individual, his or her DNA, fingerprint or retinal patterns do not change but there is some variability in their speech patterns. This variability can be used to periodically modify the individual's signature but the newly resulting signature will still be unique across the entire population.

BRIEF DESCRIPTION OF THE SEVERAL VIEWS OF THE DRAWINGS

List of Drawings

FIG. 1 Block Schematic of OMNIGENE System Operation
FIG. 2 Impedance interconnection
FIG. 3 Nucleotide (or base) circuit models
FIG. 4 Nucleotide circuit impedance
FIG. 5 Impedance expressions for doublet circuits (parallel-serial version)
FIG. 6 Impedance expressions for the codon circuit model (parallel-serial version)
FIG. 7 Impedance expressions for the doublet circuit model (serial-parallel version)
FIG. 8 Impedance expressions for the codon circuit model (serial-parallel version)
FIG. 9 Example of two user-specified input sound files and the corresponding system generated output sound files
FIG. 10 The four nucleotide sound waves generated by the nucleotide circuit model for the default sinusoidal wave input
FIG. 11 Wave, texture and signature image output for the four nucleotides
FIG. 12 Examples of wave, texture and signature image output for select codons
FIG. 13 Examples of wave, texture and signature image output for select amino acids
FIG. 14 Wave output for select diseases-amino acid and DNA versions (top and bottom rows, respectively)
FIG. 15 Texture, difference and signature images for select diseases (DNA version)
FIG. 16 Texture, difference and signature images for select diseases (amino acid version)
FIG. 17 Signatures of Cataract Genes
FIG. 18 Examples of fingerprint conversion into waves
FIG. 19 Examples of human speech converted to images
FIG. 20 Example of retinal image conversion into waves and associated signature
FIG. 21 Textured images produced by the OMNIGENE system for all 64 codons using a parallel-serial RLC circuit implementation FIG. 22 Textured images produced by the OMNIGENE system for all 64 codons using a serial-parallel RLC circuit implementation FIG. 23 Textured images produced by the system for Codon+one other input type (speech or fingerprint or retinal scan)

FIG. 24 Textured images produced by the system for Codon+two other input types (male or female speech+loop or whorl fingerprint)

FIG. 25 Textured images produced by the system for Codon+three other input types (male or female speech+loop or whorl fingerprint+retinal scan)

FIG. 26 Textured images produced by the system for Codon+two other input types [male or female speech+retinal scan+loop or whorl fingerprint)

FIG. 27 Comparative system responses to four input types [AAC codon+retinal scan+whorl fingerprint+speech (male/female)]

FIG. 28 Distinct texture patterns and signature images produced by OMNIGENE based on the first 32 codons FIG. 29 Distinct texture patterns and signature images produced by OMNIGENE based on the second 32 codons FIG. 30 Distinct texture patterns and signature images produced by OMNIGENE based on the 20 amino acids

DETAILED DESCRIPTION OF THE INVENTION

OmniGene is a software system which is used to model DNA and amino acid sequences at the electrical level using passive electrical components comprising of resistors, inductors and capacitors, hereinafter referred to as RLC circuits. The simulated circuit is subject to input signals in the form of wave patterns (either simple single frequency sinusoidal waves or signals containing a mixture of frequencies such as human speech or music) and the output response of the system is in the form of waves and images. The operational aspects of the system, as shown in FIG. 1, are as follows. In response to user input of the RLC circuit parameters, one set for each of the four nucleotides, the system generates and computes the circuit impedances for the four nucleotide circuits and circuit response for a specific frequency or set of frequencies. These circuit responses are then input into the next subsystem to generate 64 circuits ('codon' circuits) and impedance responses, one for each of the 64 codons. At the next stage of the system the 20 amino acid circuits and responses are produced. At the amino acid level each amino acid is characterized by some non-overlapping subset of the 64 codons. To obtain an amino acid's circuit impedance, the average response of the codons in the subset for the acid is computed. Each amino acid is associated with exactly one of three specific secondary structure properties—alpha helix former, beta sheet former, and helix or sheet breaker. The system then computes the average response of all amino acids associated with a particular secondary structure property. Likewise, each amino acid is characterized by exactly one of three chemical properties—acidic, basic, and neutral. The system computes the average response of all amino acids associated with a particular chemical property.

If a user inputs a DNA sequence or amino acid sequence, the system computes the overall impedance and frequency response for the entire string using the results generated at the nucleotide level or at the amino acid level.

The above system is adapted to handle user inputs involving DNA sequences, fingerprints, retinal scans and speech signals. Fingerprint and retinal scan images are first converted into wave patterns and these waves and the speech signals are input either singly or in compositions into two simulated RLC circuits—a) serial-parallel circuit version and b) parallel-serial circuit version. The wave output of these circuits is combined with the wave output of the codon circuit described in the previous paragraph to generate a wave pattern which represents the overall system response.

The wave patterns generated at different stages of the system are converted into images to provide a set of highly textured color images. In addition, each textured image is also converted into an equivalent signature image which is a solid color image representing the average color of all the pixels in the textured image.

The system also computes the difference image for any pair of textured or signature images and the difference wave for any pair of wave responses generated by the system at the various stages.

A comprehensive listing of all the mathematical formulas representing the impedances of all the circuit models used in the system are tabulated in FIGS. 2 through 8. Numerous examples of sample input and output for the system are shown in FIGS. 9 through 30. The exact captions for these figures are provided in the 'Brief Description of the Several Views of the Drawing' section of this document.

The OmniGene system is comprised of several distinct modules, each of which is associated with certain functionalities. The purpose of each of these modules and the module's input and output are briefly described in the ensuing paragraphs.

NCADATABASE( ): Set up the database containing information on nucleotides, codons, amino acids and associated probabilities for various organisms but principally homo sapiens. This module essentially sets up a set of global variables containing basic genetic information which can be accessed by a variety of other modules in the system.

DATA( ) computes, using a special resistor-capacitor (RC) electrical circuit, the sound wave patterns and textured visual representations of nucleotides, codons and amino acids based on a set of user supplied parameter values. The input parameters for the module are as follows: speech wave associated with each nucleotide, circuit parameters, steric angles of amino acids and type of biological organism. This module creates wave files, sound files and texture pattern files for each nucleotide, each codon and each amino acid.

MEANWAVE( ) is used to compute the average wave and texture response of each amino acid based on the set of codons associated with a given amino acid.

CHEMPIX( ) generates visual depictions of amino acid properties at the chemical and structural levels. At the chemical properties level, amino acids can be conveniently grouped into different categories depending on whether an amino acid is hydrophilic or hydrophobic, has a specific polarity (positive, negative or neutral), acidic, basic, aromatic, aliphatic, etc. Likewise, amino acids can be classified according to their known proclivities for forming or breaking secondary structures such as alpha helices, beta sheets, etc.

GENERATE( ) builds compositional representations of codons and DNA/RNA strings from nucleotides and genes/proteins from amino acid strings using a special set of functions. The user supplies the DNA, RNA or amino acid sequence.

MODIFY( ) computes a composite frequency response based on individual nucleotide or codon frequency functions using another special function set different from the one used in the Generate( ) module.

SIGPDB( ) creates a set of files which contain signature representations for any biological sequence.

COMPOSITE( ) generates texture and wave files for a DNA sample input into one of two special electrical circuits using resistors, inductors and capacitors (RLC circuits). One RLC circuit is a parallel-serial circuit while the other is a serial-parallel version. The resistance, inductance and capacitance values for the circuits are supplied by the user.

RLC_FP_SP_RS( ) generates texture and wave files based on fingerprint, voice print (speech sample) and retinal scan image in conjunction with the DNA-specific output generated by COMPOSITE( ). The fingerprint, retinal scan and speech data are supplied by the user.

Other modules in the system include routines to convert sound files into picture files, compare pairs of sound files or pairs of picture files, normalize sound files, and converting picture files into wave files.

The various input parameters of the OMNIGENE system are as follows: type of biological organism, the default input frequency for each nucleotide, amplitude of the sinusoidal wave signal, steric angles, biological string sequence and type of sequence (DNA or amino acid string), retinal scan image, fingerprint, and sample speech waves. For a given set of input parameter values, the OMNIGENE system outputs a set of waveforms and a set of textured images and their associated signature (solid color) images. The system has broad applications in three distinct areas:
  a) Biology, Medicine, and Pharmaceuticals
  b) Biometric Identification and Security Systems, and
  c) Household/Office Consumer Products In the area of Biology, Medicine and Pharmaceuticals, known DNA sequences and protein/gene sequences or fragments can be used as input to generate output which can be visually compared against the output generated by other actual, 'tweaked' or synthetic DNA/protein/gene sequences to see if there are distinct or noticeable differences. Tweaking a known biological sequence to study its effects is quite standard in studying the impact of gene mutations, in the custom design of pharmaceuticals, gene therapy, and in disease identification and disease treatment protocols. The DNA sequences may be obtained from any biological entity including humans, plants, animals and bacteria.

In the arena of Biometric Identification and Security Systems where access validation and verification are necessary, OMNIGENE offers at least eight (8) layers of security since the system output can be used to generate scannable ID cards. Such ID cards could contain wave, texture and signature data based on what user input is submitted to the system—DNA, DNA+fingerprint, DNA+speech, DNA+retinal scan, DNA+fingerprint+retinal scan, DNA+fingerprint+speech, DNA+speech+retinal scan, and DNA+fingerprint+retinal scan+speech. The system described in this narrative is focused on just one retinal scan and one fingerprint. However, an expanded may be obtained by using the full complement of two retinal scans and ten fingerprints of an individual.

In the area of Household/Office Consumer Products, the principal applications are in the design and manufacture of customer-specific clothing, fabric, upholstery; stationery and home/office décor such as paints and Wallpaper using the textured and signature images created by the system. This customer-specificity is possible because the input to the OMNIGENE system is based on a customer's biometric data (DNA, fingerprint, speech samples and retinal scan). If so desired, a customer could substitute/complement their speech samples with their favorite tunes. Since both speech patterns and choice of music do vary over the lifetime of an individual, this permits a certain degree of variability in the manufacturing of customer-specific products.

The invention claimed is:

1. A method for generating textured images and solid color images of the magnitude and phase responses of an interconnected set of electrical circuits which have been simulated using computer software; where each of these circuits represents a model, at the chemical structure level, of the four nucleic acid bases A, C, G and T and the codons representing the standard amino acid set {A, C, D, E, F, G, H, I, K, L, M, N, P, Q, R, S, T, V, W, Y}; where each circuit is comprised of an interconnection of resistors, inductors and capacitors; where the user specifies as basic input to the software: a) a DNA sequence or amino acid, sequence, b) a resistor value greater than zero, c) an inductor value greater than zero, d) a capacitor value greater than zero, e) a frequency value greater than zero; where the user optionally specifies as additional input any of the following: f) a speech waveform, g) a retinal scan image, and h) a fingerprint image; where for pairs of textured images or solid color images, difference images can be generated.

2. A method according to claim 1 wherein the DNA sequence or amino acid sequence represents a human gene or portion thereof.

3. A method according to claim 2 wherein the difference images generated can serve to establish the equivalence or non-equivalence of two input DNA sequences.

4. A method according to claim 2 wherein the difference images generated can serve to establish the equivalence or non-equivalence of two input amino acid sequences.

5. A method according to claim 1 wherein, given a DNA sequence $d_1 \ d_2 \ d_3 \ \ldots \ d_m$ (m>1) the circuit modeling the $i^{th}$ element (i<=m) in the DNA sequence is connected to the composite interconnected circuit modeling all the previous (i−1) elements in the input DNA sequence either in serial or in parallel fashion using an alternating pattern, thereby producing two different circuit implementations.

6. A method according to claim 1 wherein, given an amino acid sequence $a_1 \ a_2 \ a_3 \ \ldots \ a_m$ (m>1) the circuit modeling the $i^{th}$ element in the amino acid sequence is connected to the interconnected composite circuit modeling all the previous (i−1) elements in the input amino acid sequence either in serial or in parallel fashion using an alternating pattern, thereby producing two different circuit implementations.

7. A method according to claim 1 wherein the speech waveform input by the user is the user's own speech sample waveform.

8. A method according to claim 7 wherein the speech waveform is combined with the waveform generated by the interconnected circuit model of the DNA or amino-acid sequence to produce a composite waveform which is then used to generate textured images or solid images.

9. A method according to claim 1 wherein the retinal scan image input by the user is the user's own retinal image.

10. A method according to claim 9 wherein the retinal scan image is converted into a waveform.

11. A method according to claim 10 wherein the retinal waveform is combined with the waveform generated by the interconnected circuit modeling the DNA or amino-acid sequence to produce a composite waveform which is then used to generate textured images or solid images.

12. A method according to claim 1 wherein the fingerprint image input by the user is the user's own fingerprint.

13. A method according to claim 12 wherein the fingerprint image is converted into a waveform.

14. A method according to claim 13 wherein the fingerprint waveform is combined with the waveform generated by the interconnected circuit modeling the DNA or amino-acid sequence to produce a composite waveform which is then used to generate textured images or solid images.

* * * * *

SEQUENCE LISTING

```
<160> NUMBER OF SEQ ID NOS: 44

<210> SEQ ID NO 1
<211> LENGTH: 5
<212> TYPE: DNA
<213> ORGANISM: Artificial Sequence
<220> FEATURE:
<223> OTHER INFORMATION: prim_transcript

<400> SEQUENCE: 1 aaaaa                                                              5

<210> SEQ ID NO 2
<211> LENGTH: 5
<212> TYPE: DNA
<213> ORGANISM: Artificial Sequence
<220> FEATURE:
<223> OTHER INFORMATION: prim_transcript

<400> SEQUENCE: 2 aaaac                                                              5

<210> SEQ ID NO 3
<211> LENGTH: 5
<212> TYPE: DNA
<213> ORGANISM: Artificial Sequence
<220> FEATURE:
<223> OTHER INFORMATION: prim_transcript

<400> SEQUENCE: 3 aaaag                                                              5
```

```
<210> SEQ ID NO 4
<211> LENGTH: 5
<212> TYPE: DNA
<213> ORGANISM: Artificial Sequence
<220> FEATURE:
<223> OTHER INFORMATION: prim_transcript

<400> SEQUENCE: 4 aaaat                                                                  5

<210> SEQ ID NO 5
<211> LENGTH: 5
<212> TYPE: DNA
<213> ORGANISM: Artificial Sequence
<220> FEATURE:
<223> OTHER INFORMATION: prim_transcript

<400> SEQUENCE: 5 caaaa                                                                  5

<210> SEQ ID NO 6
<211> LENGTH: 5
<212> TYPE: DNA
<213> ORGANISM: Artificial Sequence
<220> FEATURE:
<223> OTHER INFORMATION: prim_transcript

<400> SEQUENCE: 6 gaaaa                                                                  5

<210> SEQ ID NO 7
<211> LENGTH: 5
<212> TYPE: DNA
<213> ORGANISM: Artificial Sequence
<220> FEATURE:
<223> OTHER INFORMATION: prim_transcript

<400> SEQUENCE: 7 taaaa                                                                  5

<210> SEQ ID NO 8
<211> LENGTH: 5
<212> TYPE: DNA
<213> ORGANISM: Artificial Sequence
<220> FEATURE:
<223> OTHER INFORMATION: prim_transcript

<400> SEQUENCE: 8 ccccc                                                                  5

<210> SEQ ID NO 9
<211> LENGTH: 5
<212> TYPE: DNA
<213> ORGANISM: Artificial Sequence
<220> FEATURE:
<223> OTHER INFORMATION: prim_transcript

<400> SEQUENCE: 9 cccca                                                                  5

<210> SEQ ID NO 10
<211> LENGTH: 5
<212> TYPE: DNA
<213> ORGANISM: Artificial Sequence
<220> FEATURE:
<223> OTHER INFORMATION: prim_transcript
```

```
<400> SEQUENCE: 10 ccccg                                                             5

<210> SEQ ID NO 11
<211> LENGTH: 5
<212> TYPE: DNA
<213> ORGANISM: Artificial Sequence
<220> FEATURE:
<223> OTHER INFORMATION: prim_transcript

<400> SEQUENCE: 11 cccct                                                             5

<210> SEQ ID NO 12
<211> LENGTH: 5
<212> TYPE: DNA
<213> ORGANISM: Artificial Sequence
<220> FEATURE:
<223> OTHER INFORMATION: prim_transcript

<400> SEQUENCE: 12 acccc                                                             5

<210> SEQ ID NO 13
<211> LENGTH: 5
<212> TYPE: DNA
<213> ORGANISM: Artificial Sequence
<220> FEATURE:
<223> OTHER INFORMATION: prim_transcript

<400> SEQUENCE: 13 gcccc                                                             5

<210> SEQ ID NO 14
<211> LENGTH: 5
<212> TYPE: DNA
<213> ORGANISM: Artificial Sequence
<220> FEATURE:
<223> OTHER INFORMATION: prim_transcript

<400> SEQUENCE: 14 tcccc                                                             5

<210> SEQ ID NO 15
<211> LENGTH: 5
<212> TYPE: DNA
<213> ORGANISM: Artificial Sequence
<220> FEATURE:
<223> OTHER INFORMATION: prim_transcript

<400> SEQUENCE: 15 ggggg                                                             5

<210> SEQ ID NO 16
<211> LENGTH: 5
<212> TYPE: DNA
<213> ORGANISM: Artificial Sequence
<220> FEATURE:
<223> OTHER INFORMATION: prim_transcript

<400> SEQUENCE: 16 gggga                                                             5

<210> SEQ ID NO 17
```

```
<211> LENGTH: 5
<212> TYPE: DNA
<213> ORGANISM: Artificial Sequence
<220> FEATURE:
<223> OTHER INFORMATION: prim_transcript

<400> SEQUENCE: 17 ggggc                                                                    5

<210> SEQ ID NO 18
<211> LENGTH: 5
<212> TYPE: DNA
<213> ORGANISM: Artificial Sequence
<220> FEATURE:
<223> OTHER INFORMATION: prim_transcript

<400> SEQUENCE: 18 ggggt                                                                    5

<210> SEQ ID NO 19
<211> LENGTH: 5
<212> TYPE: DNA
<213> ORGANISM: Artificial Sequence
<220> FEATURE:
<223> OTHER INFORMATION: prim_transcript

<400> SEQUENCE: 19 agggg                                                                    5

<210> SEQ ID NO 20
<211> LENGTH: 5
<212> TYPE: DNA
<213> ORGANISM: Artificial Sequence
<220> FEATURE:
<223> OTHER INFORMATION: prim_transcript

<400> SEQUENCE: 20 cgggg                                                                    5

<210> SEQ ID NO 21
<211> LENGTH: 5
<212> TYPE: DNA
<213> ORGANISM: Artificial Sequence
<220> FEATURE:
<223> OTHER INFORMATION: prim_transcript

<400> SEQUENCE: 21 tgggg                                                                    5

<210> SEQ ID NO 22
<211> LENGTH: 5
<212> TYPE: DNA
<213> ORGANISM: Artificial Sequence
<220> FEATURE:
<223> OTHER INFORMATION: prim_transcript

<400> SEQUENCE: 22 ttttt                                                                    5

<210> SEQ ID NO 23
<211> LENGTH: 5
<212> TYPE: DNA
<213> ORGANISM: Artificial Sequence
<220> FEATURE:
<223> OTHER INFORMATION: prim_transcript

<400> SEQUENCE: 23
```

```
tttta                                                                    5

<210> SEQ ID NO 24
<211> LENGTH: 5
<212> TYPE: DNA
<213> ORGANISM: Artificial Sequence
<220> FEATURE:
<223> OTHER INFORMATION: prim_transcript

<400> SEQUENCE: 24 ttttc                                                                    5

<210> SEQ ID NO 25
<211> LENGTH: 5
<212> TYPE: DNA
<213> ORGANISM: Artificial Sequence
<220> FEATURE:
<223> OTHER INFORMATION: prim_transcript

<400> SEQUENCE: 25 ttttg                                                                    5

<210> SEQ ID NO 26
<211> LENGTH: 5
<212> TYPE: DNA
<213> ORGANISM: Artificial Sequence
<220> FEATURE:
<223> OTHER INFORMATION: prim_transcript

<400> SEQUENCE: 26 atttt                                                                    5

<210> SEQ ID NO 27
<211> LENGTH: 5
<212> TYPE: DNA
<213> ORGANISM: Artificial Sequence
<220> FEATURE:
<223> OTHER INFORMATION: prim_transcript

<400> SEQUENCE: 27 ctttt                                                                    5

<210> SEQ ID NO 28
<211> LENGTH: 5
<212> TYPE: DNA
<213> ORGANISM: Artificial Sequence
<220> FEATURE:
<223> OTHER INFORMATION: prim_transcript

<400> SEQUENCE: 28 gtttt                                                                    5

<210> SEQ ID NO 29
<211> LENGTH: 4
<212> TYPE: DNA
<213> ORGANISM: Artificial Sequence
<220> FEATURE:
<223> OTHER INFORMATION: prim_transcript

<400> SEQUENCE: 29 aaag                                                                     4

<210> SEQ ID NO 30
<211> LENGTH: 4
<212> TYPE: DNA
```

```
<213> ORGANISM: Artificial Sequence
<220> FEATURE:
<223> OTHER INFORMATION: prim_transcript

<400> SEQUENCE: 30 aatg                                                                    4

<210> SEQ ID NO 31
<211> LENGTH: 4
<212> TYPE: DNA
<213> ORGANISM: Artificial Sequence
<220> FEATURE:
<223> OTHER INFORMATION: prim_transcript

<400> SEQUENCE: 31 agaa                                                                    4

<210> SEQ ID NO 32
<211> LENGTH: 4
<212> TYPE: DNA
<213> ORGANISM: Artificial Sequence
<220> FEATURE:
<223> OTHER INFORMATION: prim_transcript

<400> SEQUENCE: 32 agat                                                                    4

<210> SEQ ID NO 33
<211> LENGTH: 4
<212> TYPE: DNA
<213> ORGANISM: Artificial Sequence
<220> FEATURE:
<223> OTHER INFORMATION: prim_transcript

<400> SEQUENCE: 33 attt                                                                    4

<210> SEQ ID NO 34
<211> LENGTH: 4
<212> TYPE: DNA
<213> ORGANISM: Artificial Sequence
<220> FEATURE:
<223> OTHER INFORMATION: prim_transcript

<400> SEQUENCE: 34 cttt                                                                    4

<210> SEQ ID NO 35
<211> LENGTH: 4
<212> TYPE: DNA
<213> ORGANISM: Artificial Sequence
<220> FEATURE:
<223> OTHER INFORMATION: prim_transcript

<400> SEQUENCE: 35 gtaa                                                                    4

<210> SEQ ID NO 36
<211> LENGTH: 4
<212> TYPE: DNA
<213> ORGANISM: Artificial Sequence
<220> FEATURE:
<223> OTHER INFORMATION: prim_transcript

<400> SEQUENCE: 36 tcta                                                                    4
```

```
<210> SEQ ID NO 37
<211> LENGTH: 4
<212> TYPE: DNA
<213> ORGANISM: Artificial Sequence
<220> FEATURE:
<223> OTHER INFORMATION: prim_transcript

<400> SEQUENCE: 37 tgcc                                                                       4

<210> SEQ ID NO 38
<211> LENGTH: 5
<212> TYPE: DNA
<213> ORGANISM: Artificial Sequence
<220> FEATURE:
<223> OTHER INFORMATION: prim_transcript

<400> SEQUENCE: 38 ttttc                                                                      5

<210> SEQ ID NO 39
<211> LENGTH: 21
<212> TYPE: DNA
<213> ORGANISM: Artificial Sequence
<220> FEATURE:
<223> OTHER INFORMATION: prim_transcript

<400> SEQUENCE: 39
ctgactcctg aggagaagtc t                                                   21

<210> SEQ ID NO 40
<211> LENGTH: 21
<212> TYPE: DNA
<213> ORGANISM: Artificial Sequence
<220> FEATURE:
<223> OTHER INFORMATION: prim_transcript

<400> SEQUENCE: 40
ctgactcctg tggagaagtc t                                                   21

<210> SEQ ID NO 41
<211> LENGTH: 18
<212> TYPE: DNA
<213> ORGANISM: Artificial Sequence
<220> FEATURE:
<223> OTHER INFORMATION: prim_transcript

<400> SEQUENCE: 41
atcatctttg gtgtttcc                                                       18

<210> SEQ ID NO 42
<211> LENGTH: 15
<212> TYPE: DNA
<213> ORGANISM: Artificial Sequence
<220> FEATURE:
<223> OTHER INFORMATION: prim_transcript

<400> SEQUENCE: 42
atcatcggtg tttcc                                                          15

<210> SEQ ID NO 43
<211> LENGTH: 12
<212> TYPE: DNA
<213> ORGANISM: Artificial Sequence
<220> FEATURE:
```

-continued

```
<223> OTHER INFORMATION: prim_transcript

<400> SEQUENCE: 43
gctgccaatg gt                                                              12

<210> SEQ ID NO 44
<211> LENGTH: 12
<212> TYPE: DNA
<213> ORGANISM: Artificial Sequence
<220> FEATURE:
<223> OTHER INFORMATION: prim_transcript

<400> SEQUENCE: 44
gctgccagtg gt                                                              12
```